US011761938B2

(12) United States Patent
Potyrailo et al.

(10) Patent No.: US 11,761,938 B2
(45) Date of Patent: Sep. 19, 2023

(54) SENSING SYSTEM AND METHOD

(71) Applicant: General Electric Company, Schenectady, NY (US)

(72) Inventors: Radislav Alexandrovich Potyrailo, Niskayuna, NY (US); Douglas Forman, Niskayuna, NY (US); Steven Go, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 508 days.

(21) Appl. No.: 16/448,328

(22) Filed: Jun. 21, 2019

(65) Prior Publication Data
US 2020/0400635 A1 Dec. 24, 2020

(51) Int. Cl.
*G01N 33/00* (2006.01)
*G01N 27/02* (2006.01)
(Continued)

(52) U.S. Cl.
CPC ....... *G01N 33/0073* (2013.01); *B64C 39/024* (2013.01); *G01N 27/028* (2013.01);
(Continued)

(58) Field of Classification Search
CPC .. G01N 33/0073; G01N 27/028; G05D 1/101; G05D 1/0206; G05D 1/0278;
(Continued)

(56) References Cited

U.S. PATENT DOCUMENTS 5,927,648 A 7/1999 Woodland et al.
8,426,813 B2 4/2013 Furry
(Continued)

FOREIGN PATENT DOCUMENTS

CN 102980977 A 3/2013
CN 203439256 U 2/2014
CN 205691166 U 11/2016
(Continued)

OTHER PUBLICATIONS

Cooks et al., "Detection Technologies. Ambient mass spectrometry", Science, vol. No. 311, pp. 1566-1570, Mar. 17, 2006.
(Continued)

*Primary Examiner* — Jeff A Burke
*Assistant Examiner* — Sihar A Karwan
(74) *Attorney, Agent, or Firm* — Fletcher Yoder, P.C.

(57) ABSTRACT

A sensor system includes an unmanned vehicle system is provided that includes a housing, and an environmental sensor system coupled to the housing, the environmental sensor system configured to detect one or more environmental conditions of an environment in operational contact with the unmanned vehicle system. The environmental sensor includes a sensing element that includes a sensing material to detect and quantify at least one analyte gas by measuring impedance of the sensing element at one or more frequencies of the different frequencies during exposure of the sensing material to the at least one analyte gas. A control unit includes one or more processors coupled with the environmental sensor and configured to receive a detector signal from the detector circuit of the environmental sensor indicative of the one or more environmental conditions, and control the movement of the unmanned vehicle system based on an operation signal of a remote device, instructions received at a vehicle controller, the detector signal, or in response to detected route conditions.

37 Claims, 20 Drawing Sheets

(51) Int. Cl.
  G05D 1/10 (2006.01)
  G05D 1/02 (2020.01)
  B64C 39/02 (2023.01)
  G05D 1/00 (2006.01)

(52) U.S. Cl.
  CPC .......... G05D 1/0011 (2013.01); G05D 1/021 (2013.01); G05D 1/0206 (2013.01); G05D 1/0278 (2013.01); G05D 1/101 (2013.01); G05D 2201/0207 (2013.01)

(58) Field of Classification Search
  CPC ............... G05D 1/0011; G05D 1/021; G05D 2201/0207; G05D 1/0094; B64C 39/024; B64C 2201/12
  See application file for complete search history.

(56) References Cited

U.S. PATENT DOCUMENTS

| | | | |
|---|---|---|---|
| 8,560,146 B2 | 10/2013 | Kwon et al. | |
| 8,820,672 B2 | 9/2014 | Erben et al. | |
| 9,162,753 B1 | 10/2015 | Panto et al. | |
| 9,513,635 B1 | 12/2016 | Bethke et al. | |
| 9,606,028 B2 | 3/2017 | Detweiller et al. | |
| 9,639,091 B2 | 5/2017 | Carpenter | |
| 10,008,373 B1* | 6/2018 | Carr | G01R 33/0035 |
| 2016/0202225 A1 | 7/2016 | Feng et al. | |
| 2016/0214715 A1 | 7/2016 | Meffert | |
| 2016/0304217 A1* | 10/2016 | Fisher | B64F 1/222 |
| 2016/0376000 A1* | 12/2016 | Kohstall | B63G 8/08 |
| | | | 114/313 |
| 2017/0003684 A1 | 1/2017 | Knudsen | |
| 2017/0124885 A1 | 5/2017 | Patterson et al. | |
| 2018/0080890 A1* | 3/2018 | Potyrailo | H04Q 9/00 |
| 2018/0080891 A1* | 3/2018 | Potyrailo | G01N 27/04 |
| 2019/0204265 A1* | 7/2019 | Stowell | C01B 32/182 |

FOREIGN PATENT DOCUMENTS

| | | |
|---|---|---|
| CN | 106970554 A | 7/2017 |
| KR | 101653280 B1 | 9/2016 |

OTHER PUBLICATIONS

Allen et al., "Measurements of Methane Emissions at Natural Gas Production Sites in the United States", Proceedings of the National Academy of Sciences of the United States of America, vol. No. 110, Issue No. 44, pp. 17768-17773, Sep. 16, 2013.

Wolfbeis., "Editorial: Probes, Sensors, and Labels: Why is Real Progress Slow?", Angewandte Chemie International Edition, vol. No. 52, pp. 9864-9865, 2013.

Zhang et al., "Applications of Absorption Spectroscopy Using Quantum Cascade Lasers", Applied Spectroscopy , vol. No. 68, Issue: 10, pp. 1095-1107, 2014.

McManus et al., "Recent Progress in Laser-Based Trace Gas Instruments: Performance and Noise Analysis", Applied Physics B, vol. No. 119, Issue: 01, pp. 203-218, Apr. 2015.

Villa et al., "An Overview of Small Unmanned Aerial Vehicles for Air Quality Measurements: Present Applications and Future Prospectives", Sensors, vol. No. 16, Issue: 07, pp. 1-29, 2016.

Emran et al., "Low-Altitude Aerial Methane Concentration Mapping", Remote Sensors, vol. 9, Issue: 08, pp. 1-13, 2017.

* cited by examiner

SENSING SYSTEM AND METHOD

GOVERNMENT LICENSE RIGHTS

This invention was made with government support under contract number NIOSH 211-2015-63806 awarded by the GOVT. The government has certain rights in the invention.

FIELD

One or more embodiments are disclosed that relate to systems and methods for sensing analytes in gases.

BACKGROUND

Chemical monitoring of environments with mobile unmanned platforms such as aerial, ground-based, above-ground-based, under-ground-based, under-water-based and other platforms can potentially provide the ability to map the spatial distribution of pollutants of interest in the presence of uncontrolled ambient background. Examples of scenarios where such chemical monitoring is of particular importance include monitoring of industrial above- and under-ground production sites, urban monitoring, and many others. However, to provide the needed value, this environmental or industrial monitoring should be performed with an adequate level of detection selectivity without false negative or false positive readings of pollution levels.

This type of detection selectivity has been achieved using laboratory-based sophisticated analytical instruments. For laboratory applications, instruments based on gas chromatography (GC), mass spectrometry (MS), ion mobility spectrometry (IMS), and tunable diode laser absorption spectroscopy (TDLAS) are preferred over non-selective conventional sensors to provide the needed detection selectivity despite their relatively high power consumption, high cost, and large size. These and other classic analytical instruments need either a vacuum pump, a carrier gas and/or a line power or a significant battery to operate. Applications in portable formats are not practical, with the limitations including needing a large battery or power source, inability to selectively detect multiple analyte gases, and high cost. These instruments are inconvenient, but are the only alternative to existing sensor systems that suffer from the lack of selective gas responses.

Equipping an unmanned miniature platform with such instruments provides difficulties because of the weight restrictions that require at 10-1,000 times less weight and 100-10,000 times less power that the existing instruments that provide needed detection selectivity.

BRIEF DESCRIPTION

In one embodiment, a sensor system is provided that includes an unmanned vehicle system that has an environmental sensor system configured to detect one or more environmental conditions of an environment in operational contact with the electronic device. The environmental sensor includes a sensing element that includes a sensing material and electrodes configured to apply electrical stimuli to the sensing material at different frequencies, and a detector circuit configured to detect and quantify at least one analyte gas by measuring impedance of the sensing element at one or more frequencies of the different frequencies during exposure of the sensing material to the at least one analyte gas. The detector circuit is configured to control one or more of a low detection range of the sensing material to at least one analyte gas, a high detection range of the sensing material to the at least one analyte gas, a response linearity of the sensing material to the at least one analyte gas, a dynamic range of measurements of the at least one analyte gas by the sensing material, or a rejection of one or more interfering gases by the sensing material. The unmanned vehicle system also includes a control unit comprising one or more processors communicatively coupled with the environmental sensor, the one or more processors are configured to receive a detector signal from the detector circuit of the environmental sensor indicative of the one or more environmental conditions, and receive an operation signal from a remote device to control the movement of the unmanned vehicle system based on the operation signal and the detector signal.

In one embodiment, a sensor system is provided that includes an unmanned vehicle system for determining environmental conditions having a housing including at least one propeller, at least one motor for driving a propeller, and a vehicle controller electrically coupled to the at least one motor and configured to receive command signals from a remote device to control the operation of the at least one motor and direction of the unmanned vehicle system. An environmental sensor system is coupled to the housing and includes a sensing element that includes a sensing material and electrodes configured to apply electrical stimuli to the sensing material at different frequencies, and a detector circuit configured to detect and quantify at least one analyte gas by measuring impedance of the sensing element at one or more frequencies of the different frequencies during exposure of the sensing material to the at least one analyte gas. The detector circuit is configured to control one or more of a low detection range of the sensing element to at least one analyte gas, a high detection range of the sensing element to the at least one analyte gas, a response linearity of the sensing element to the at least one analyte gas, a dynamic range of measurements of the at least one analyte gas by the sensing element, or a rejection of one or more interfering gases by the sensing element. A control unit is coupled to the environmental sensor and includes one or more processors communicatively coupled with the environmental sensor and the vehicle controller. The one or more processors are configured to receive an environmental signal from the detector circuit of the environmental sensor system indicative of the at least one analyte gas.

In one embodiment, a method of collecting environmental conditions is provided that includes positioning a vehicle including an environmental sensor system to detect an environmental condition, and applying electrical stimuli at different frequencies with the environmental sensor system, the environmental sensor system comprising a sensing element that includes a sensing material and electrodes. A detector circuit measures impedance of the sensing element at one or more frequencies of the different frequencies during exposure of the sensing material to at least one analyte gas, wherein the detector circuit is configured to detect and quantify the at least one analyte gas. The method also includes controlling one or more of a low detection range of the sensing element to the at least one analyte gas, the high detection range of the sensing element to the at least one analyte gas, a response linearity of the sensing element to the at least one analyte gas, a dynamic range of measurements of the at least one analyte gas by the sensing element, or a rejection of one or more interfering gases by the sensing element with the detector circuit.

DETAILED DESCRIPTION

Figure 1:
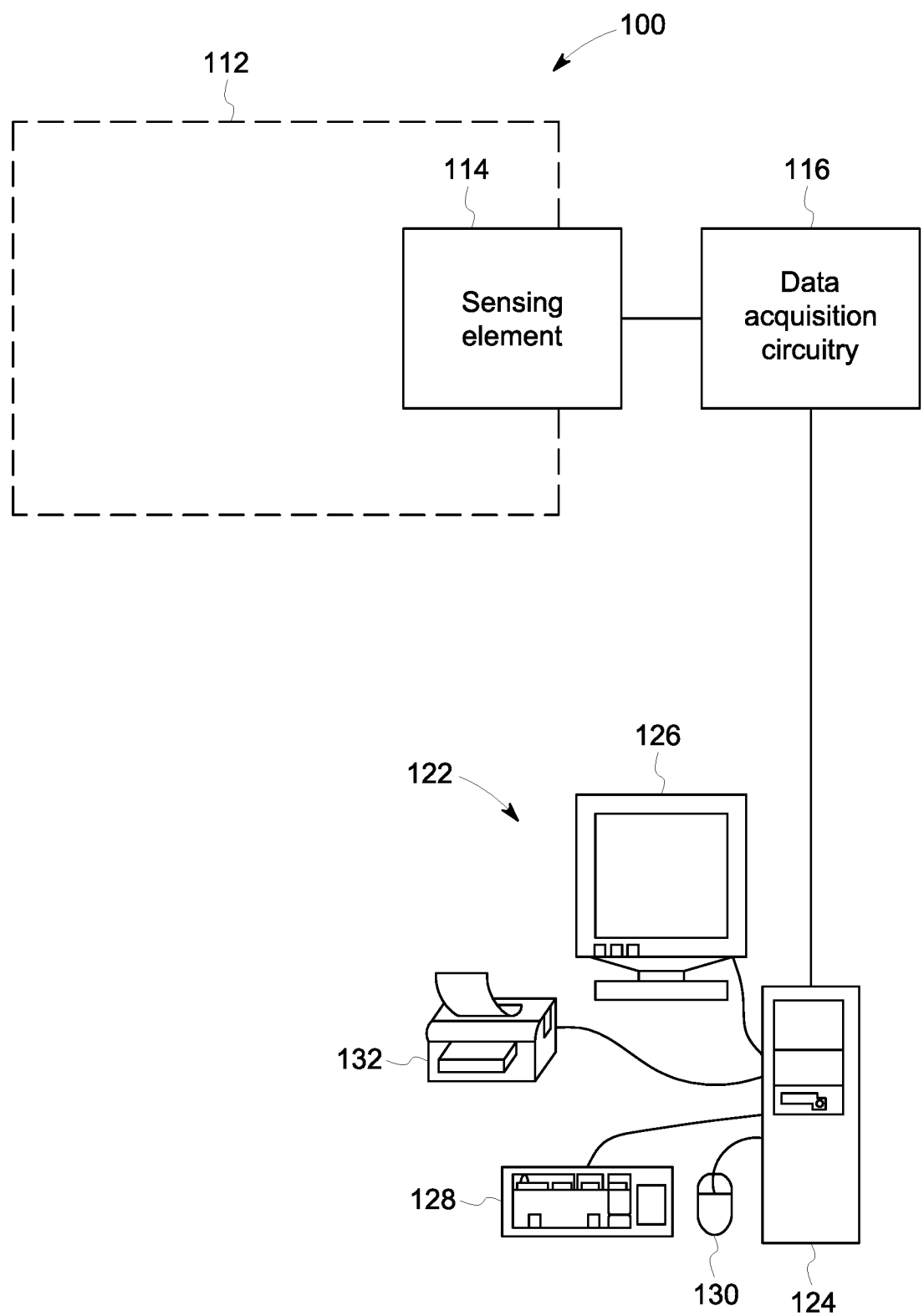
FIG. 1 illustrates a sensor system according to one or more embodiments.

One or more embodiments of the inventive subject matter described herein provide for sensor systems and methods that operate a gas impedance sensor with controlled sensor response selectivity and linearity. The systems and methods can control operation of the sensor system so that the sensor system is more responsive (e.g., sensitive to and/or able to measure) to one or more analytes of interest than other analytes of interest at different times or under different operating conditions. The systems and methods can control operation of the sensor system so that the output of the sensor system (e.g., the measurements of the analyte(s) of interest, as expressed in terms of measured impedance of a sensing material of the sensor) is linear with respect to different amounts of the analyte(s) of interest.

The sensing material of the sensor can be a metal oxide in one embodiment, due to the ability of a sensing element of the sensor system to detect numerous, different gases of interest using such a sensing material. The systems and methods change electrical properties of the sensing element by coupling one or more passive electrical components to the sensor system with the sensor system performing impedance measurements over a broad frequency range or at a single frequency. Systems and methods set forth below have unexpectedly changed the frequency position of the relaxation frequency of the dielectric relaxation region of the frequency response of the sensor system over several orders of magnitude, allowing frequency matching with the operational frequency range of impedance analyzer components where the impedance analyzer components have very low operation power, for example 60 mW or less, 10 mW or less, 2 mW or less. The impedance analyzer components can have the size of 10 mm×10 mm×5 mm, 5 mm×5 mm×2 mm, 1 mm×1 mm×0.5 mm. The impedance analyzer components can operate at multiple frequencies or can operate only at several predetermined frequencies or only at one predetermined frequency. The systems and methods can unexpectedly perform measurements at a single frequency with an improved sensor system selectively relative to performing measurements at a single frequency without the need for scanning across several frequencies. The selectivity of the sensor system includes the ability of the system to respond to an analyte gas of interest and not to respond to other gases presented to the system either separately or in a mixture with the analyte gas of interest. The linearity of the system to an analyte gas includes a deviation of an experimentally determined calibration straight line from an ideal straight target line. The calibration of the system includes the relationship between the analyte gas concentration and the system response signal to determine performance characteristics of the system (dynamic range, response linearity, low detection range, high detection range, and others). The dynamic range of the sensor includes measurements of analyte gas in the analyte gas concentration range between the lowest and the highest concentrations of the analyte gas that can be quantified by the sensor.

Sensing materials of the inventive subject matter described herein, when probed by impedance spectroscopy, exhibit a relaxation region in their impedance spectra. Both, the real part of the impedance and the imaginary part of the impedance have a relaxation region. This relaxation region can be determined by examining the real part of the measured impedance of the sensing material as a function of frequency to locate where the real part of the impedance changes from high impedance value and zero slope at low frequencies to decreasing impedance values with a relatively high slope at higher frequencies and to decreasing impedance values with a relatively low slope at even higher frequencies, and where impedance values are approaching zero at the highest frequencies. Alternatively, the relaxation region can be determined by examining the imaginary part of the measured impedance of the sensing material to locate where the curvature of the imaginary part of the impedance changes from a concave shape to a convex shape, or from a convex shape to a concave shape. The imaginary part of impedance exhibits a peak in negative direction that is known as a relaxation peak of the relaxation region of the imaginary part of the impedance spectrum of a sensing material. The frequency at which the relaxation peak of the imaginary part of the impedance spectrum reaches its negative maximum is known as characteristic relaxation frequency.

At least one technical effect of the sensor system and methods described herein include the use of the sensor systems for detection of gases of interest in various environments, and optionally the actions that are implemented in response to the detection of a gas of interest by the systems. For example, the systems and methods described herein can be used for the monitoring of leaks in underground mines, as well as in gas-production and gas-distribution facilities, monitoring of urban pollution in intelligent cities, monitoring of gases in compressors, engines, and turbines, monitoring of gases in industrial and consumer assets, and monitoring of gases in headspace in bioprocess applications of cell culture manufacturing runs. Examples of gases for detection in this invention include reducing gases, oxidizing gases, volatile organic compounds, combustible gases, toxic gases, volatile pollutants, and any other gases. To this end the UMV system may perform at least one of gas leaks surveillance, gas pollution surveillance, industrial monitoring, environmental monitoring, urban monitoring, traffic pollution monitoring, homeland security monitoring, military monitoring, or search and rescue monitoring In order to monitor for leaks, urban pollution, the presence of methane, and the like, unmanned vehicles (UMVs) are provided that house the sensor system described herein. By using an UMV that is remotely controlled by an individual, the UMV may provide sensing in locations that are difficult and unsafe for an individual. The UMVs may include drones, aquatic vehicles, land and underground vehicles, or the like. The sensor system is both exceptionally sensitive and accurate at detecting specific analyte gases and fluids while also being extremely light weight, allowing for coupling to the UMVs. Additionally, to assist in enhancing detection, the UMVs may vary their course based on the analyte detection to receive a more accurate detection of the analyte of interest. An UMV can be also remotely controlled by a navigation system that does not include a human input but rather uses the destination coordinates of the targeted region and the real-time coordinates of the UMV to guide the UMV to the destination coordinates. The destination coordinates may be in any known form such as map, GPS or others.

FIG. 1 illustrates a sensor system 100 for detection and quantification of at least one analyte gas according to one embodiment of the inventive subject matter set forth herein. The system 100 examines a fluid sample in contact with the system 100 for detection of one or more analyte gases of interest therein. This fluid may be a gas or fuel, such as a hydrocarbon-based fuel. One example of the fluid is natural gas that is supplied to a powered system (e.g., a vehicle, or a stationary generator set) for consumption. Other examples of such a fluid can include gasoline, diesel fuel, jet fuel or kerosene, bio-fuels, petrodiesel-biodiesel fuel blends, natural gas (liquid or compressed), and fuel oils. Another example of the fluid is outdoor or indoor ambient air. Another example of the fluid is ambient air with relatively small concentrations of hydrocarbons and/or other pollutants. Another example of the fluid is at least one gas dissolved in an industrial liquid such as transformer oil, bioprocess media, fermentation media, wastewater, and any other. Another example of the fluid is the at least one gas dissolved in a consumer liquid such as milk, non-alcoholic beverages, alcoholic beverages, cosmetics, and any other. Another example of the fluid is at least one gas dissolved in a body liquid such as blood, sweat, tears, saliva, urine, and any other. Another example of the fluid is one or more of at least one gas pollutants, multiple gases pollutants, volatiles, volatiles from drug manufacturing, volatiles from manufacturing of improvised explosive devices, particle matter contaminants.

The system 100 includes a fluid reservoir 112 for holding the sample and one or more sensing elements 114 at least partially disposed in, on, or within the fluid reservoir 112. Alternatively, the sensing element 114 may be set in a flow path of the fluid outside of the reservoir 112, such as coupled to in-line connectors in fluid communication with the fluid reservoir that define a flow path. In one embodiment, the sensing element 114 may provide continuous monitoring of the fluid within the reservoir or flow path. In one embodiment, the one or more sensing elements 114 may be impedance gas sensors, or some alternative sensors. The fluid reservoir 112 may be in a form of a vessel with controlled volume or in a form of an open area such as an indoor facility (e.g., a room, a hall, a house, a school, a hospital, or the like), or in a form of an outdoor facility (e.g., a stadium, a gas-production site, a seashore, a forest, or the like).

The sensing element 114 may detect characteristics or properties of the fluid via a resonant or non-resonant impedance spectral response. One or more of the inductor-capacitor-resistor resonant circuits (LCR resonators) may measure the resonant impedance spectral response. A non-resonant impedance spectral response is measured when the circuit does not contain an inductor. The resonant or non-resonant impedance spectrum of the sensing element 114 in proximity to the fluid sample varies based on sample composition and/or components. The measured resonant or non-resonant impedance values Z' (which may be the real part of resonant impedance, Zre) and Z" (which may be the imaginary part of resonant impedance, Zim) reflect the response of the sensing element 114 to the fluid or fluid sample.

Other embodiments of the inventive subject matter described herein include other designs of sensors besides resonant and non-resonant impedance sensors. Other sensors can be capacitor sensors, electro-mechanical resonator sensors (e.g., tuning forks, cantilever sensors, acoustic device sensors), thermal sensors, optical sensors, acoustic sensors, photoacoustic sensors, near-infrared sensors, ultraviolet sensors, infrared sensors, visible light sensors, fiber-optic sensors, reflection sensors, multivariable sensors, or single-output sensors. The sensor may generate electrical or optical output responses upon exposure to a measured sample. The sensor may be a bio-inspired optical sensor that may be fabricated using conventional photolithography and chemical etching techniques with formed layers of horizontal lamella supported by the vertical ridge.

An electrical field may be applied to a sensing material or film of the sensing element 114 via electrodes. The distance between the electrodes, may define the magnitude of the electric field applied to the sensing element 114 (e.g., to the sensing material or film). The electrodes may be in direct contact with the sensing material. For example, the sensing element 114 may be a combination of a sensing region and associated circuits and/or the sensing region may be coated with the sensing material. The sensing material may be semiconductor material or metal oxide material.

Data from the sensing element 114 may be acquired via data acquisition circuitry 116, which may be associated with the sensor or which may be associated with a control system, such as a controller or workstation 122 including data processing circuitry, where additional processing and analysis may be performed. The controller or workstation 122 may include one or more wireless or wired components, and may also communicate with the other components of the system 100. Suitable communication models include wireless or wired. At least one suitable wireless model includes radio frequency devices, such as radio frequency identification (RFID) wireless communications. Other wireless communication modalities may be used based on application specific parameters. For example, where there may be electromagnetic field (EMF) interference, certain modalities may work where others may not. The data acquisition circuitry 116 optionally can be disposed within the sensing element 114. Other suitable locations may include disposition being within the workstation 122. Further, the workstation 122 can be replaced with a control system of the whole process where the sensor and its data acquisition circuitry may be connected to the control system of process.

The data acquisition circuitry 116 may be in the form of a sensor reader, which may be configured to communicate wirelessly or wired with the fluid reservoir 112 and/or the workstation 122. The fluid reservoir 112 may be an ambient open outdoor environment limited by the Earth atmosphere and by the distance that the UMV may be capable to move per its power supply level. For example, the sensor reader may be a battery-operated device and/or may be powered using energy available from the main control system or by using harvesting of energy from ambient sources (light, vibration, heat, or electromagnetic energy).

Additionally, the data acquisition circuitry may receive data from one or more sensing elements 114 (e.g., multiple sensors positioned at different locations in or around the fluid reservoir). The data, including environmental data of a detector signal may be stored in short or long term memory storage devices, such as archiving communication systems, which may be located within or remote from the system and/or reconstructed and displayed for an operator, such as at the operator workstation. The sensing element 114 may be positioned on or in fuel or fluid reservoirs, associated piping components, connectors, flow-through components, and any other relevant process components. The sensors may be positioned outdoors or indoors for monitoring of thermogenic and biogenic leaks and emissions. The sensors may be positioned outdoors or indoors for monitoring of unauthorized activities such as burning waste without permit, smoking in unapproved areas, chemical processing of raw ingredients to produce illegal substances, and other unauthorized activities. The sensors may be positioned in industrial, urban, residential, public, medical, military facilities and other facilities outdoors or indoors for gas monitoring. The data acquisition circuitry 116 may include one or more processors for analyzing the data received from the sensing element 114. For example, the one or more processors may be one or more computer processors, controllers (e.g., microcontrollers), or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed and/or stored in the hardware of the one or more processors.

In addition to displaying the data, the operator workstation 122 may control the above-described operations and functions of the system 100. The operator workstation 122 may include one or more processor-based components, such as general purpose or application-specific computers or processors 124. In addition to the processor-based components, the computer may include various memory and/or storage components including magnetic and optical mass storage devices, internal memory, such as RAM chips. The memory and/or storage components may be used for storing programs and routines for performing the techniques described herein that may be executed by the operator workstation 122 or by associated components of the system 100. Alternatively, the programs and routines may be stored on a computer accessible storage and/or memory remote from the operator workstation 122 but accessible by network and/or communication interfaces present on the computer 124. The computer 124 may also comprise various input/output (I/O) interfaces, as well as various network or communication interfaces. The various I/O interfaces may allow communication with user interface devices, such as a display 126, keyboard 128, electronic mouse 130, and printer 132, that may be used for viewing and inputting configuration information and/or for operating the imaging system. Other devices, not shown, may be useful for interfacing, such as touchpads, heads up displays, microphones, and the like. The various network and communication interfaces may allow connection to both local and wide area intranets and storage networks as well as the Internet. The various I/O and communication interfaces may utilize wires, lines, or suitable wireless interfaces, as appropriate or desired. In one embodiment, the operator workstation 122 can be miniaturized to be in a form of a handheld device. In one embodiment, the operator workstation 122 can be miniaturized to be in a form of a wearable device. In one embodiment, the operator workstation 122 can be miniaturized to be in a form of an implantable device. In one embodiment, the operator workstation 122 can be miniaturized to be integrated in an unmanned vehicle such as a drone, a robot or any other unmanned vehicle. In one embodiment, the operator workstation 122 can be miniaturized to be integrated in a vehicle for machine inspection of an industrial site or an industrial structure or a process area that may be performed by the human or machine operator positioned on a ground or airborne. Non-limiting examples of positions on the ground include standing, walking, or driving. Non-limiting examples of airborne positions include flying, flying by a fixed wing platform, or flying by an air-drone platform. Non-limiting examples of machine inspection include inspection by robots, drones, unmanned vessels, and unmanned vehicles. Non-limiting examples of drones include airborne, ground-based, and subsea drones. In an embodiment, the industrial site is a site along a gas or oil pipeline, gas or oil production site, gas or oil distribution site, and/or gas or oil transport site.

The terms "industrial site" or "industrial structure" or "process area" as used herein includes a naturally occurring site or structure or area that is used for industrial applications or an artificial site or structure or area produced by any industry or industrial company that is used for industrial, environmental, recreational, residential, military, security, health, sports and other applications. Non-limiting examples of an industrial site include manufacturing facility, processing facility, disposal facility, industrial research facility, gas producing facility, oil producing facility, residential facility, sports facility, military facility, security facility, and others. In an aspect, the condition of the industrial site is based on the concentration of the external contaminant in the industrial fluid. Non-limiting examples of external contaminants include methane, ethane, hydrocarbon, ethylene, acetylene, water. In one embodiment, the operator workstation 122 can have a wired or wireless connectivity to a central station. A central station can be in a form of a network server or a remote server where such a server can be hosted on the Internet. This central station can store, manage, and process data collected from at least one sensor.

Figure 2A:
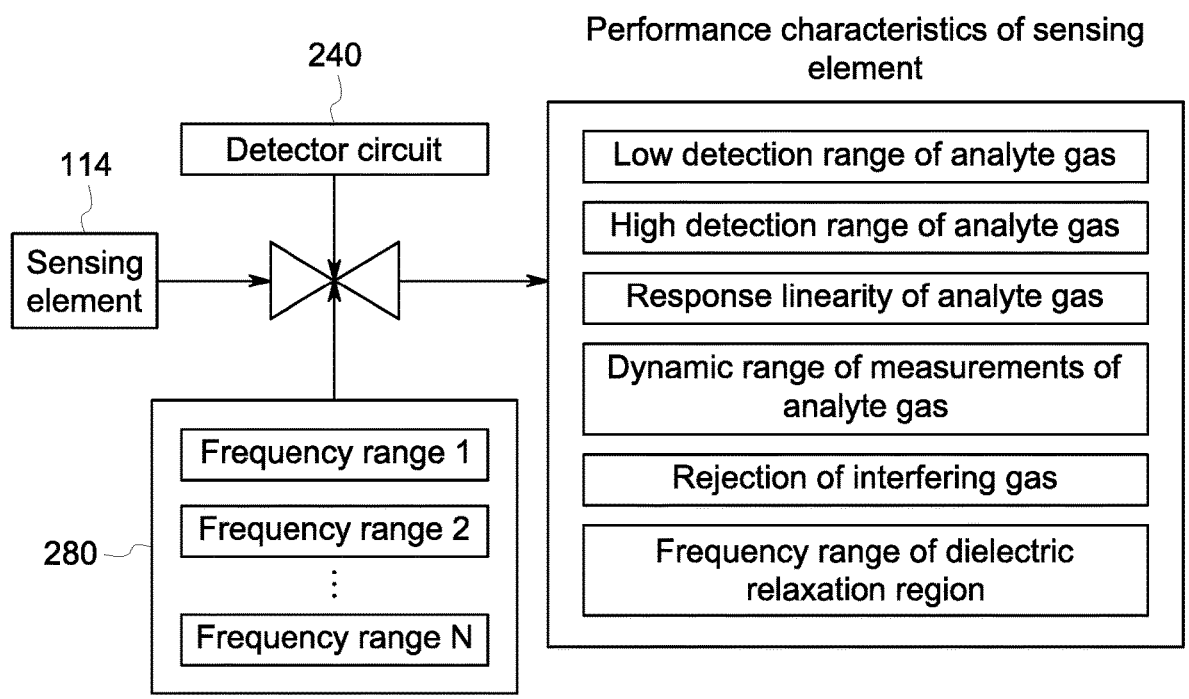
FIG. 2A illustrates one example of the sensor system shown in FIG. 1 for the detection and quantification of at least one analyte gas according to one or more embodiments.

FIG. 2A illustrates one example of the sensor system 100 shown in FIG. 1 for the detection and quantification of at least one analyte gas. In the system 100, the sensing element 114 has a dielectric substrate having a sensing electrode structure. The sensing electrode structure of the sensing element 114 may be connected to the data acquisition circuitry 116. The sensing electrode structure can be coated with a sensing material. The sensing electrode structure, with the sensing material, forms a sensing region circuit. The sensing electrode structure, with the sensing material that forms the sensing region circuit, may operationally contact a sample that contains one or more analyte gases or contaminants.

Suitable interdigital electrode structures for probing a fluid sample include two- and four-electrode structures. Suitable materials for electrodes include stainless steel, platinum, gold, noble metals, and others. Suitable electrodes may be formed using metal etching, screen-printing, ink-jet-printing, and mask-based metal deposition techniques. The thickness of fabricated electrodes on the substrates may be in the range from about 10 nanometers to about 1000 micrometers. The materials for the interdigital electrode structures, substrate, sensing layer, and electrode formation methods may be selected based at least in part on the application specific parameters. Suitable materials of the dielectric substrate may include silicon dioxide, silicon nitride, alumina, ceramics, and others. The sensing electrode structure of the dielectric substrate includes a semiconducting sensing material deposited on at least a portion of the electrode structure. Optionally, suitable examples of sensing materials or coatings include semiconducting materials, n-type semiconducting materials, p-type semiconducting materials, metal oxides, composite materials, inorganic materials, organic materials, polymeric materials, formulated materials, nano-composites, or the like. For example, in one or more embodiments described herein, the semiconducting sensing material may be tin dioxide $SnO2$ or any alternative material.

The sensing element 114 is connected to a detector circuit 240. The detector circuit 240 includes one or more passive and/or active electrical components. Nonlimiting examples of passive electrical components are resistors, resistive elements, capacitors, capacitive elements, transformers, inductors, or the like. Nonlimiting examples of active components are transistors, diodes, and the like. The detector circuit 240 is configured to detect and quantify at least one analyte gas by measuring the impedance of the sensing element 114 at one or more different frequencies 280 (e.g., frequency range 1, frequency range 2, frequency range N) during exposure of the sensing material to the analyte gas. For example, the one or more frequencies 280 may correspond to a frequency response range or a discrete frequency response characteristic of an impedance analyzer circuit 314.

Measurements of the impedance of the sensing element 114 may be performed at a single frequency, at discrete frequencies, or at multiple scanned frequencies by the impedance analyzer circuit 314 where the impedance analyzer circuit 314 may be part of the detector circuit 240, conductively coupled with the sensing element 114. Measurements of one or more of the real $Z'$ or imaginary $Z''$ parts of the impedance of the sensing element 114 may be performed within a dielectric relaxation region of the sensing element. The dielectric relaxation region of the sensing element 114 may be a range of frequencies within a designated threshold of the measured impedance of the sensing element 114 at the occurrence of relaxation peak and/or a relaxation point frequency or an inflection point frequency range of the imaginary $Z''$ part of the impedance. For example, the relaxation peak (also known as relaxation frequency) may be identified as the location along the imaginary part of an impedance spectra at which the impedance response changes from being concave to convex, or changes from being convex to concave. The inflection point frequency is the frequency or the frequency range at which the inflection point occurs. Alternatively, the inflection point can be determined be examining the real part of the measured impedance of the sensing material 308 to locate where the curvature of the real part of the impedance changes from a concave shape to a convex shape, or from a convex shape to a concave shape.

The detector circuit 240 controls the performance characteristics of the sensing element 114. This control may include control of a low detection range of the sensing element to the analyte gas, a high detection range of the sensing element to the analyte gas, a response linearity of the sensing element to the analyte gas, a dynamic range of measurements of the analyte gas by the sensing element, a rejection of one or more interfering gases by the sensing element, a frequency range of the dielectric relaxation region of the sensing element 114, or a combination of one or more thereof.

Performance characteristics of the impedance analyzer circuit 314 include the frequency range of the impedance measurements measured by the impedance analyzer. Additionally or alternatively, other performance characteristics of the impedance analyzer circuit 314 include an amount of power required for operation, the size of the impedance analyzer circuit, the cost of the impedance analyzer circuit, or the like. The performance characteristics of the impedance analyzer circuit 314 may be matched with the performance characteristics of the sensing element 114. For example, such matching may be the range of the impedance magnitude that is produced by the sensing element 114 that is measured by the impedance analyzer circuit 314. Additionally or alternatively, such matching may be the frequency range of the dielectric relaxation region that is produced by the sensing element and that needs to be measured by the impedance analyzer circuit 314. These nonlimiting examples will be discussed in more detail below.

Additionally or alternatively, the performance characteristics of the sensing element 114 may be matched with the performance characteristics of the impedance analyzer circuit 314. For example, such matching may be a frequency range of the dielectric relaxation region that is produced by the sensing element 114 and that can be measured by the impedance analyzer circuit 314. Additionally or alternatively, such matching may be the power required for operation of the sensor system 100.

Figure 2B:
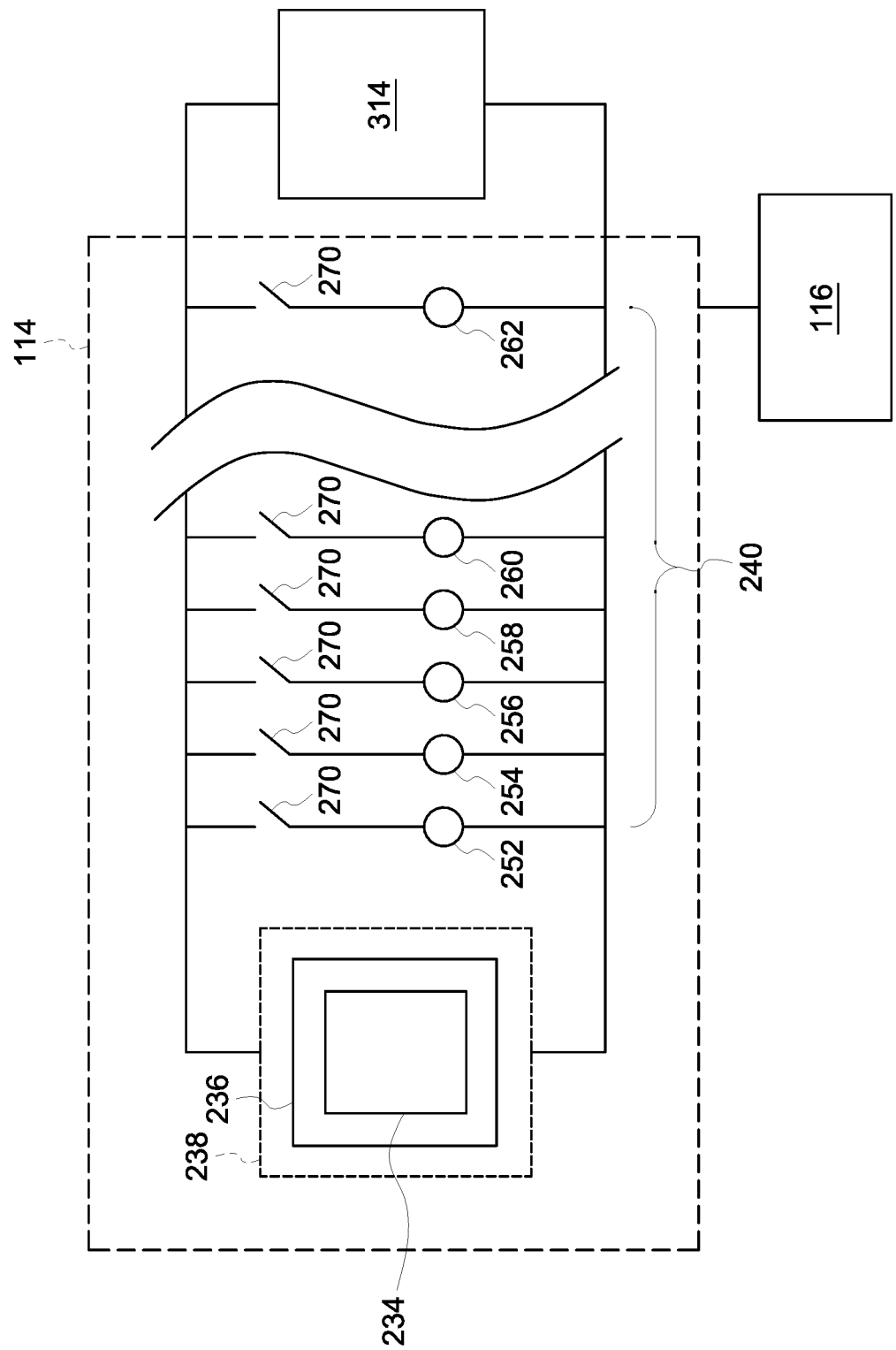
FIG. 2B illustrates one example of a schematic of the sensor system of FIG. 2A for detection and quantification of at least one analyte gas according to one or more embodiments.

FIG. 2B illustrates one example of a schematic of the sensor system 100 of FIG. 2A for detection and quantification of at least one analyte gas. Optionally, the sensor system 100 may have an alternative configuration. The sensing electrode structure 234, with the sensing material 236, forms the sensing region circuit 238 of the sensing element 114. The system 100 measures a resistance value ($R_{MOS}$) and capacitance value ($C_{MOS}$) of the sensing region circuit 238 to obtain the sensor response upon exposure of the sensing element 114 to the one or more analyte gases, ambient gases, or contaminants of the sample. For example, the sensing region circuit 238 includes at least one resistive element and at least one capacitive element that are used to measure the $R_{MOS}$ and $C_{MOS}$. Optionally, the sensing region circuit 238 may include multiple resistive elements, capacitive elements, or the like.

The sensing element 114 is conductively or galvanically or directly coupled with the impedance analyzer circuit 314 having one or more processors that include one or more microprocessors, field programmable gate arrays, and/or integrated circuits. The one or more processors of the impedance analyzer circuit 314 receives an electrical signal from the sensing element 114 that represents the impedance of a sensing material during exposure of the sensing material to the fluid sample. The processors 314 examine the impedance response of the sensing material in order to determine the presence and/or amount (e.g., concentration) of one or more analyte gases in the environment to which the sensing material is exposed, as described herein.

The impedance analyzer circuit 314 may provide scanning capability to measure sensor impedance across a predetermined frequency range. Alternatively, impedance analyzer circuit 314 may provide the capability to measure sensor impedance at discrete determined frequencies or at a single at determined frequency.

The detector circuit 240 is integrally coupled with the sensing region circuit 238 and the impedance analyzer circuit 314. The detector circuit 240 has at least one passive electrical component electrically connected with the sensing region circuit 238. In the illustrated embodiment, the detector circuit includes six different passive electrical components (252, 254, 256, 258, 260, 262) connected in parallel with the sensing region circuit 238 as shown in FIG. 2B.

Alternatively, more than six or less than six different passive and/or active electrical components may be included with the detector circuit 240. For example, the detector circuit 240 may include 10, 25, 50, 100, 500, or the like, different passive and/or active electrical components. Optionally, one or more passive and/or active electrical components of the detector circuit 240 may be connected in parallel with one or more different passive and/or active electrical components. For example, the passive electrical components 252, 254 may be connected in parallel, and may be connected in series with the passive components 256, 258, 260, 262. Optionally, one or more passive and/or active electrical components may be arranged in any alternative configuration.

Each of the passive electrical components (252, 254, 256, 258, 260, 262) include switches 270 that allow each passive electrical component to selectively couple with the sensing circuit region 238 and the impedance analyzer circuit 314. Additionally, each passive electrical component may be selectively disconnected from the sensing region circuit 238. For example, one or more processors of the data acquisition circuitry 116 may direct the switches 270 of one or more of the passive electrical components (e.g., 252, 254, 256, and 258) to remain open, and may direct the switches 270 of one or more of the passive electrical components (e.g., 260, 262) to close, thereby electrically disconnecting the passive electrical components 252, 254 256, 258 from the sensing region circuit 238 and electrically connecting the passive electrical components 260, 262 with the sensing region circuit 238.

The passive electrical components 252, 254, 256, 258, 260, 262 may be capacitive elements and each may have a capacitance value that changes the capacitance of the sensing element 114 when one or more of the capacitive elements are electrically coupled to the sensing region circuit 238. For example, one or more of the capacitive elements may have a unique or a same capacitance value. In the illustrated embodiment, and as described herein, the capacitance values may be 10 picofarad pF (component 252), 47 pF (component 254), 100 pF (component 256), 470 pF (component 258), and 1000 pF (component 260). Optionally, the component 262 may have a capacitance value that is the same (e.g., 100 pF) or unique (4700 pF) to the capacitance values of the other components.

The passive electrical components 252, 254, 256, 258, 260, 262 change position of the relaxation region of impedance spectra Z' and Z" of the sensing element 114 when one or more of the passive electrical components are electrically or galvanically coupled to the sensing region circuit 238.

Position of the relaxation region of impedance spectra Z' and Z" may be changed by adding a capacitor to the sensing region circuit 238.

The non-limiting range at which the passive electrical components change the range of the capacitance of the sensing element 114 includes from about 0.01 pF to about 100,000 pF, from about 0.1 pF to 10,000 pF, from about 1.0 pF to about 10,000 pF, from about 10 pF to about 10,000 pF, or the like. Changing the capacitance of the sensing element 114 allows the passive electrical components to match a frequency response range or a discrete frequency response of the impedance analyzer circuit 314 that is integrally coupled with the detector circuit 240 within a dielectric relaxation region of the sensing element 114. For example, the passive electrical component may match a frequency response of the impedance analyzer circuit 314 over low and/or high frequencies of operation. The non-limiting examples of frequency ranges may be from about 100 Hz to about 100,000,000 Hz, from about 1,000 Hz to about 1,000,000 Hz, from about 1,000 Hz to about 100,000 Hz, from 10,000 Hz to about 1,000,000 Hz, or any combinations thereof therein. The non-limiting examples of discrete (e.g., single) frequencies may be about 200 Hz, about 1,000 Hz, about 5,000 Hz, about 10,000 Hz, about 100,000 Hz, about 1,000,000 Hz, or any other discrete frequency therein. Changing the capacitance of the sensing element 114 allows the impedance analyzer circuit 314 to perform measurements at frequency range of interest or at a discrete frequency of interest with an improved sensor selectivity to the analyte of interest over the conventional system that is does not change the capacitance of the sensing element. As shown in FIG. 2A, passive elements can be connected in parallel to the sensing region circuit 238. Additionally or alternatively, passive elements can be connected in series to the sensing region circuit 238. Passive elements can be also resistors to adjust the magnitude of the impedance spectra Z' and Z". The non-limiting range at which the passive electrical components change the range of the resistance of the sensing element 114 and/or the sensing region circuit 238 includes from about 1 Ohm to about 1,000,000,000 Ohm, from about 10 Ohm to about 1,000,000 Ohm, from about 100 Ohm to about 100,000 Ohm, or the like.

Figure 3:
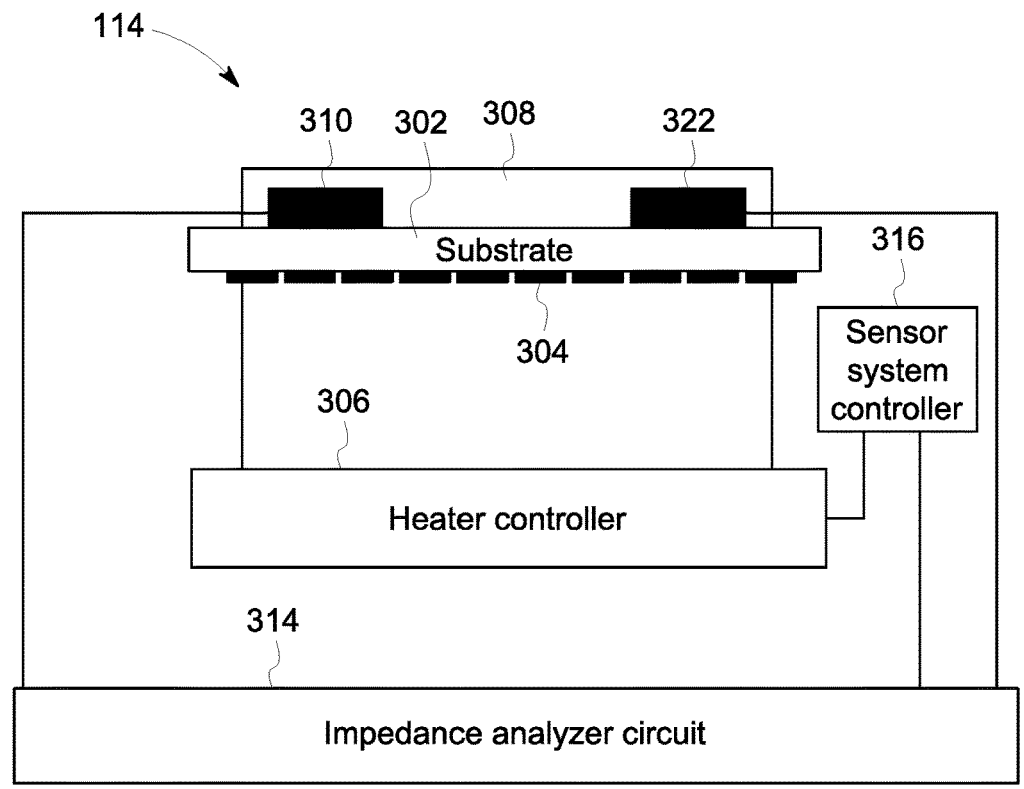
FIG. 3 illustrates another example of a sensing element of the sensor system shown in FIG. 1 according to one or more embodiments.

FIG. 3 illustrates another example of the sensing element 114. The sensing element 114 includes a dielectric substrate 302, such as a dielectric material. One or several heating elements 304, such as high resistance bodies, are coupled to one side of the dielectric substrate 302. The heating elements 304 receive electric current from a heater controller 306, which represents hardware circuitry that conducts the heater current or voltage to the heating elements 304 to heat the dielectric substrate 302 and to heat a sensing material or film 308 that is coupled to the other side of the dielectric substrate 302 and to electrodes 310 and 322. The sensor system 100 operates at a constant temperature of the sensing element 114. For example, the temperature of the sensing material 308 is constant and is not varied during measurements by the sensing element 114. In one or more embodiments of the inventive subject matter described herein, the sensing material 308 utilizes a metal oxide sensing film and may be measured at particular frequencies that control one or more of a low detection range of the sensing element to at least one analyte gas, a high detection range of the sensing element to the at least one analyte gas, a response linearity of the sensing element to the at least one analyte gas, a dynamic range of measurements of the at least one analyte gas by the sensing element, or a rejection of one or more interfering gases by the sensing element.

The sensing material 308 can include one or more materials deposited onto the dielectric substrate 302 to perform a function of predictably and reproducibly affecting the impedance sensor response upon interaction with the environment. For example, a metal oxide such as SnO2 may be deposited as the sensing material 308.

Sensing electrodes 310, 322 are coupled with or disposed in the sensing material 308 and are located on the dielectric substrate 302 in the illustrated embodiment. The sensing electrodes 310, 322 are conductive bodies that are conductively coupled with the impedance analyzer circuit 314. The impedance analyzer circuit 314 may provide scanning capability to measure sensor impedance across a predetermined frequency range. Alternatively, the impedance analyzer circuit 314 may provide the capability to measure sensor impedance at discrete determined frequencies or at a single frequency. Discrete determined frequencies can be equally spaced from each other or non-equally spaced from each other. Discrete determined frequencies can be generated without or with a specific increasing or decreasing frequency order. A sensor system controller 316 directs the impedance analyzer circuit 314 on what frequencies of a frequency to apply for interrogation of the sensing film or sensing material 308 and what integration time to apply to measure the sensor response at each frequency. Additionally, sensor system controller 316 directs heater controller 306 on what voltage or power to apply to heating elements 304 or to what temperature to bring the heating elements 304. For example, the heating elements 304 heat the sensing material 308 to a first temperature that is kept constant or substantially constant and is not varied as the impedance analyzer circuit 314 measures the impedance of the sensing element 114. In one or more embodiments, the multivariable gas sensor 114 operates at a temperature of at least 50° C. above an ambient temperature. Optionally, the sensor 114 may operate at a temperature greater than and/or less than 50° C. above and/or below the ambient temperature. In one embodiment, the system may measure an impedance (f) (represented by Eq. (1)) of exposure of the sensing material or film of the sensor to a sample while the sensing material or film is excited with electric stimuli and heated:

$$(f) = Z_{re}(f) + jZ_{im}(f) \qquad \text{Eq. (1)}$$

where $Z_{re}(f)$ may be the real part of the impedance and $Z_{im}(f)$ may be an imaginary part of the impedance. In one embodiment, the real part of the impedance $Z_{re}(f)$ and imaginary part of the impedance $Z_{im}(f)$ may be two components of a non-resonant impedance (f). In one embodiment, the real part of the impedance $Z_{re}(f)$ and imaginary part of the impedance $Z_{im}(f)$ may be two components of a resonant impedance (f). In one embodiment, the resonant impedance spectral response of the sensor may be a multivariable resonant response as more than one frequency may be utilized to measure sensor response across the resonance of the sensor. In some embodiments, the resonant impedance response of the sensor may be a multivariable resonant response because more than one frequency may be utilized to measure sensor response outside the resonance peak of the sensor. In some embodiments, the sensor response may be measured at multiple frequencies across the resonance of the sensor. For example, if the sensing element with the electrodes coated with the sensing film resonates at about 10 MHz, the measured frequencies and associated sensor responses may be measured from about 8 MHz to about 12 MHz. This multivariable resonant response may be analyzed by multivariate analysis.

A sensor can refer to a multivariable sensor capable of producing multiple response signals that are not substantially correlated with each other and where these individual response signals from the multivariable sensor are further analyzed using multivariate analysis tools to construct response patterns of sensor exposure to different analytes at different concentrations. In one embodiment, multivariable or multivariate signal transduction is performed on the multiple response signals using multivariate analysis tools to construct a multivariable sensor response pattern. A multivariate analysis can refer to a mathematical procedure that is used to analyze more than one variable from the sensor response and to provide the information about the type of at least one gas from the measured sensor parameters and/or to quantitative information about the concentration of at least one gas from the measured sensor parameters. Non-limiting examples of multivariate analysis tools include canonical correlation analysis, regression analysis, nonlinear regression analysis, principal components analysis, discriminate function analysis, multidimensional scaling, linear discriminate analysis, logistic regression, or neural network analysis.

Additional non-limiting examples of multivariate analysis tools include machine learning tools such as supervised learning tools, un-supervised learning tools, semi-supervised learning tools, reinforcement learning tools, and deep learning tools. A conventional sensor can be converted into a multivariable sensor by measuring more than one response such as response signals, that are not substantially correlated, with each other and where individual response signals from the sensor are further analyzed using multivariate analysis tools.

One or more embodiments of the sensor system described herein can incorporate the sensing element 114 having the detector circuit 240, where the sensing element 114 is operably connected to the impedance analyzer circuit 314. The impedance analyzer circuit 314 measures the response of the sensor to different gases, where the range of frequencies for gas analysis is selected to be at frequencies around the inflection point of the imaginary part of the impedance spectrum of the sensor. The inflection point of the imaginary part of the impedance spectrum is also known as the relaxation peak of the relaxation region of the imaginary part of the impedance spectrum of the sensing material. The detector circuit 240 changes the capacitance of the sensing element 114 in order to change the frequency range and/or discrete frequency of the sensing element 114 to match range of frequencies or discrete frequency of interest of the impedance analyzer circuit 314 based on the different gases, as described below. For example, the one or more passive electrical components of the detector circuit 240 control the dielectric relaxation region of the sensing element 114. As used herein, the term "impedance spectral response" may be referred to as "impedance response," "multivariable resonant response," "resonant impedance spectra," and/or variations thereof.

In one or more embodiments described herein, the impedance analyzer circuit 314 provides an improved sensor response selectivity and linearity upon exposure to different gases over the conventional measurements of the sensor and where the sensor includes the one or more sensing materials 308. The sensing materials 308 may be one or more of dielectric polymers, conducting polymers, metal oxides, catalytic metals, macrocycles, cage compounds, carbon allotropes, ionic liquids, composite materials, semiconductors, semiconducting nanowires, functionalized metal nanoparticles, or the like.

Figure 4:
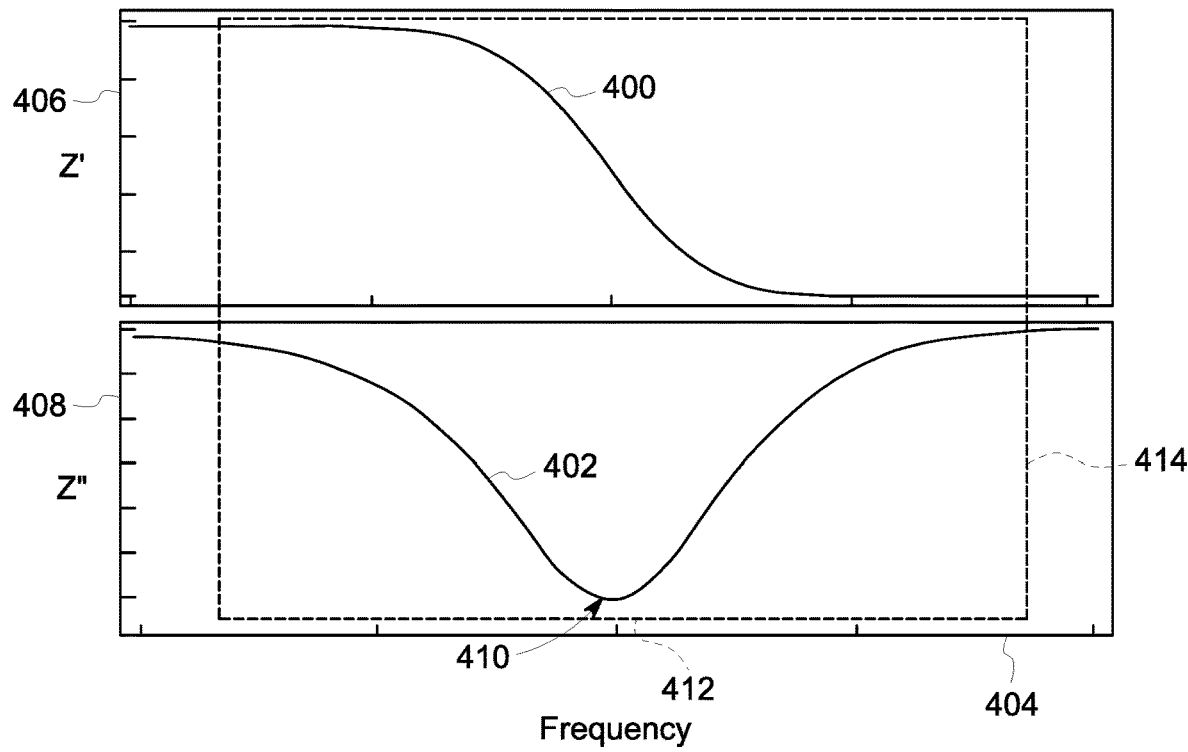
FIG. 4 illustrates impedance measurements of a sensing material of the sensor shown in FIGS. 1-3 according to one embodiment of the inventive subject matter described herein.

FIG. 4 illustrates impedance measurements 400, 402 of the sensing material 308 of the sensor 114 (as shown in FIG. 3) according to one embodiment of the inventive subject matter described herein. The measurements 400, 402 are shown alongside a horizontal axis 404 representative of frequencies at which the electric current is supplied to the sensing material 308 via the electrodes 310, 322. The measurements 400 are shown alongside a vertical axis 406 representative of the magnitude of the real part of the measured impedance and the measurements 402 are shown alongside a vertical axis 808 representative of the magnitude of the imaginary part of the measured impedance.

The imaginary part of the impedance response 402 of the sensor 114 includes an inflection point 410. This inflection point 410 is associated with an inflection point frequency 412 along the horizontal axis 404. The inflection point 410 can be identified as the location along the imaginary part of the impedance response 402 at which the response 402 changes from being concave to convex, or changes from being convex to concave. The inflection point frequency 412 is the frequency at which the inflection point 410 occurs. The inflection point of the imaginary part of the impedance spectrum is the relaxation peak of the relaxation region of the imaginary part of the impedance spectrum of a sensing material. The relaxation peak of the imaginary part of the impedance spectrum reaches its negative maximum at a frequency known as characteristic relaxation frequency.

The system 100 can control the sensor 114 to apply the electric stimuli (e.g., electric current) to the sensing material 308 via the electrodes 310, 322 at frequencies that are lower or that are higher than the inflection point frequency 412. Additionally, the system 100 can control the sensor 114 to apply the electric stimuli (e.g., electric current) to the sensing material 308 via the electrodes 310, 322 at a frequency at about the inflection point frequency 412. Additionally, the system 100 can control the sensor 114 to apply the electric stimuli (e.g., electric current) to the sensing material 308 via the electrodes 310, 322 at a frequency at about the inflection point frequency 412. For example, the data acquisition circuitry 116 can control the sensor 114 to only apply current to the sensing material 308 via the electrodes 310, 322 at frequencies that are larger than the inflection point frequency 412. In one embodiment, the sensor 114 is controlled to only apply current to the sensing material 308 via the electrodes 310, 322 at frequencies that are smaller than the inflection point frequency 412 and that are within a designated frequency range 414 that includes some, but not all, of the frequencies that are smaller than the inflection point frequency 412. The sensor 114 can be prevented (e.g., by the data acquisition circuitry 116) from applying electric current to the sensing material 308 via the electrodes 310, 322 at frequencies that are at or above the inflection point frequency in one embodiment. Nonlimiting examples of the frequency position of the relaxation peak of the relaxation region of the imaginary part of the impedance spectrum of a sensing material can be 10 Hz to 100 Hz, 100 Hz to 1000 Hz, 1 kHz to 10 kHz, 10 kHz to 100 kHz, 1000 kHz to 10 MHz, 10 MHz to 100 MHz, 1000 MHz to 1 GHz, or the like.

In another embodiment, the sensor 114 is controlled to only apply current to the sensing material 308 via the electrodes 310, 322 at frequencies that are larger than the inflection point frequency 412 and that are within a designated frequency range that includes some, but not all, of the frequencies that are greater than the inflection point frequency. The sensor 114 can be prevented (e.g., by the data acquisition circuitry 116) from applying electric current to the sensing material 308 via the electrodes 310, 322 at frequencies that are at or below the inflection point frequency 412 in one embodiment.

In another embodiment, the sensor 114 is controlled to only apply current to the sensing material 308 via the electrodes 310, 322 at frequencies that are at about the inflection point frequency 412 and that are within a designated frequency range that includes some, but not all, of the frequencies that are at about the inflection point frequency 412. The sensor 114 can be prevented (e.g., by the data acquisition circuitry 116) from applying electric current to the sensing material 308 via the electrodes 310, 322 at frequencies that are far from the inflection point frequency 412 in one embodiment.

Figure 5:
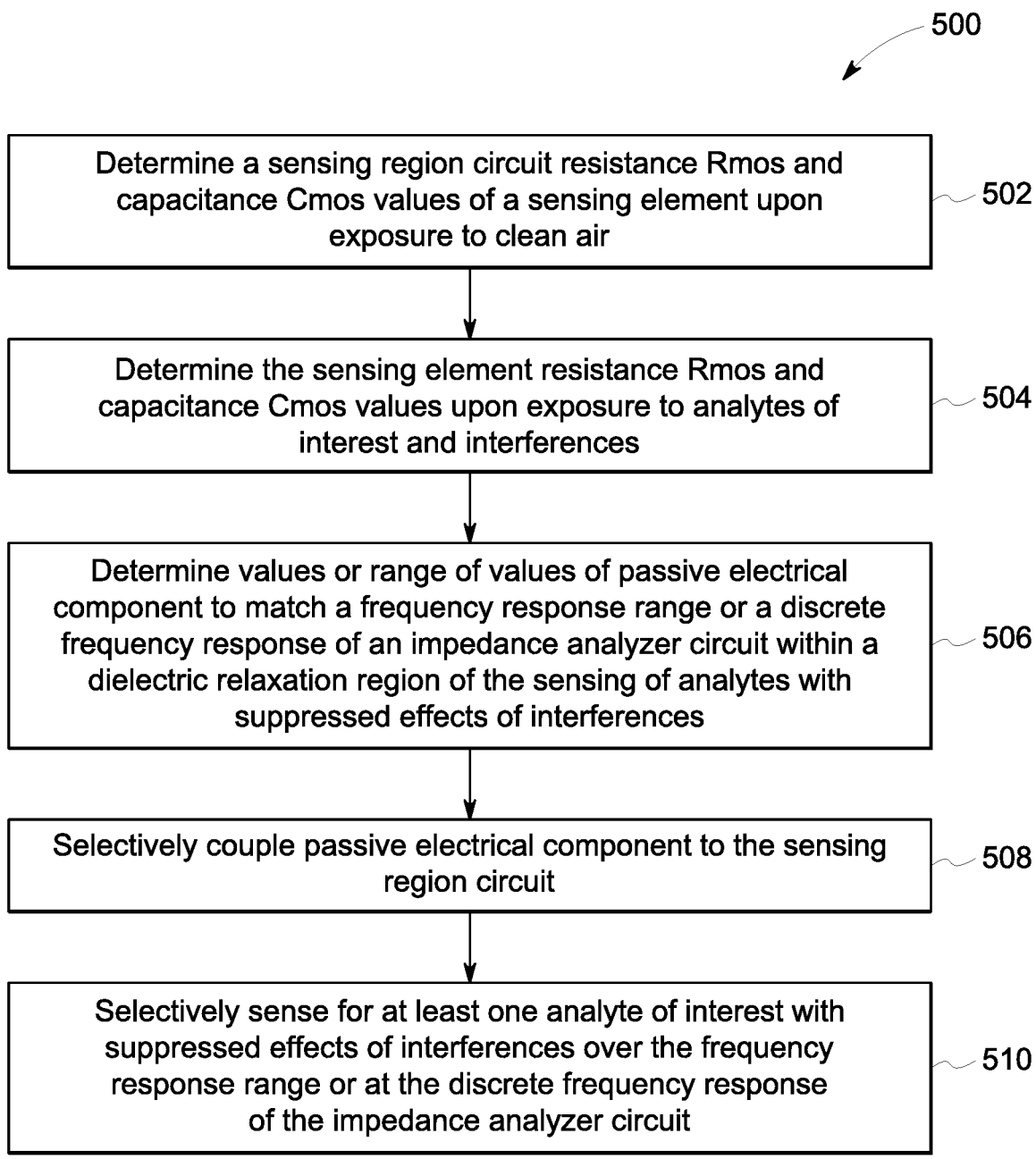
FIG. 5 illustrates a flowchart of one embodiment of a method for detecting and quantifying one or more analytes in a sample using a sensing element according to one or more embodiments.

FIG. 5 illustrates a flowchart of one embodiment of a method 500 for measuring one or more analytes of interest in a sample using an impedance gas sensor. The method 500 can represent the operations performed by the sensor system 100 and the sensing element 114 described herein, or optionally can represent the operations performed by another sensing system and/or another gas sensor. For example, the method 500 can represent operations performed by the system 100 and/or sensing element 114 under direction of one or more software applications, or optionally can represent an algorithm useful for writing such software applications.

At 502, resistance $R_{MOS}$ and capacitance $C_{MOS}$ properties of the sensing element 114 are measured during exposure of the sensing element 114 to a first gas sample. In one embodiment, this gas sample is clean air, such as air that does not include an analyte of interest sought to be measured in another, different sample (e.g., methane, ethane, or another hydrocarbon). For example, the clean air does not include interference gases. The sensing element 114 can apply electric current to the sensing material 308 via the electrodes 310, 322 while the sensing material 308 is exposed to (e.g., placed into contact with) the gas sample at a variety of frequencies.

At 504, the resistance $R_{MOS}$ and capacitance $C_{MOS}$ properties of the sensing element 114 are measured during exposure of the sensing element 114 to a second gas sample. In one embodiment, this gas sample is an analyte of interest, such as methane, ethane, or another hydrocarbon. Nonlimiting examples of analytes of interest include reducing gases, oxidizing gases, volatile organic compounds, combustible gases, toxic gases, volatile pollutants, and any other gases of interest. The sensing element 114 can apply electric current to the sensing material 308 via the electrodes 310, 322 while the sensing material 308 is exposed to (e.g., placed into contact with) the gas sample at a variety of different frequencies.

At 506, a capacitance value or a range of capacitance values of one or more passive electrical components (e.g., capacitive elements) are determined in order to change a capacitance of the sensing element 114 to match a frequency range or a discrete frequency response of the impedance analyzer circuit 314 within a dielectric relaxation region of the sensing element 114. Changing the capacitance of the sensing element 114, that is coupled with the impedance analyzer circuit 314, allows the impedance analyzer circuit 314 to selectively sense an analyte of interest (e.g., methane, ethane, another hydrocarbon, hydrogen, carbon monoxide, or the like) with suppressed effects of interferences.

At 508, the capacitance of the sensing element 114 is changed by selectively coupling one or more of the passive electrical components 252, 254, 256, 258, 260, 262 of the detector circuit 240 to the sensing region circuit 238. For example, the data acquisition circuitry 116 can communicate a control signal to the sensing element 114 to direct one or more of the switches 270 of one or more of the passive electrical components to open or close in order to change the capacitance of the sensing element 114. The detector circuit 240 controls one or more of the low detection range of the sensing material 308 to the analyte gas, the high detection range of the sensing material 308 to the analyte gas, the response linearity of the sensing material 308 to the analyte gas, the dynamic range of measurements of the analyte gas by the sensing material 308, the rejection of one or more interfering gases by the sensing material 308 as the detector circuit 240 operates at a designated frequency of the different frequencies for measuring impedance of the sensing element 114.

At 510, selective sensing of one or more analytes of interest is performed using the sensing element 114 operating within a dielectric relaxation region of the sensing element in order to match a discrete frequency response or a frequency response range of the impedance analyzer circuit 314. For example, the sensing material 308 of the sensing element 114 can be exposed to a gas sample potentially having one or more analytes of interest therein. The data acquisition circuitry 116 can communicate a control signal to the sensing element 114 to direct the sensing element 114 to apply electric current to the sensing material 308 via the electrodes 310, 322 either over a designated frequency response range or at the designated discrete frequency of the impedance analyzer circuit 314 that is within the dielectric relaxation region of the sensing element 114. Operating the sensing element 114 at these frequencies can increase the selective sensing of the sensing element 114 (e.g., the sensitivity of sensing of the sensing element 114) to one or more analytes of interest in the sample relative to one or more other analytes (and relative to operating the sensing element 114 at a different frequency or different frequency range of the impedance analyzer circuit 314). The sensitivity of the sensing element 114 includes a measured sensor response signal per analyte concentration unit.

Additionally, the data acquisition circuitry 116 can communicate a control signal to the sensor 114 to direct the sensor 114 to apply electric current to the sensing material 308 via the electrodes 310, 322 at frequencies that are lower than or greater than the inflection point frequency 412. Operating the sensor 114 over the broad range of frequencies can provide a response pattern of sensing of multiple gases with one sensor 114. Such response pattern of sensing of multiple gases with one sensor cannot be achieved by operating only at the frequencies that are lower than the inflection point frequency 412, or operating only at the frequencies that are higher than the inflection point frequency 412, or operating only at the inflection point frequency 412. Such response pattern of sensing multiple gases can be further analyzed using multivariate analysis tools or machine learning tools to accurately quantify individual gases.

Additionally, operating the sensing element 114 at frequencies higher than the inflection point frequency 412 can suppress the effects of interferences. For example, the sensing element 114 can be less sensitive to gases such as interference or interfering gases other than the analytes of interest when operating within the dielectric relaxation region of the sensing element 114 (relative to operating the sensing element 114 at a frequency outside of the dielectric relaxation region of the sensing element 114). Operating the sensing element 114 within dielectric relaxation range can increase the linearity of the response of the sensing element 114 to the one or more analytes of interest relative to operating the sensing element 114 at a frequency outside of the dielectric relaxation region. The term "interference" or "interferent" as used herein includes any substance or chemical constituent or physical constituent that undesirably affects quality of measurements of the analyte by reducing the accuracy, precision, or other known parameters of measurements of the analyte by the sensing element 114.

Optionally, the sensor 114 can be operated at a single frequency that is smaller or greater than the inflection point frequency 412. For example, instead of conducting the electric current to the sensing material 308 via the electrodes 310, 322 at multiple, different frequencies that are smaller than the inflection point frequency 412, the current can be conducted to the sensing material 308 at a single frequency that is smaller than the inflection point frequency 412. For example, instead of conducting the electric current to the sensing material 308 at multiple, different frequencies that are greater than the inflection point frequency 412, the current can be conducted to the sensing material 308 via the electrodes 310, 322 at a single frequency that is greater than the inflection point frequency 412.

In another embodiment method, one or more passive electrical components (e.g., resistive elements) can be implemented. Resistive elements can be used to change the magnitude of the relaxation region of impedance spectra Z' and Z".

Figure 6:
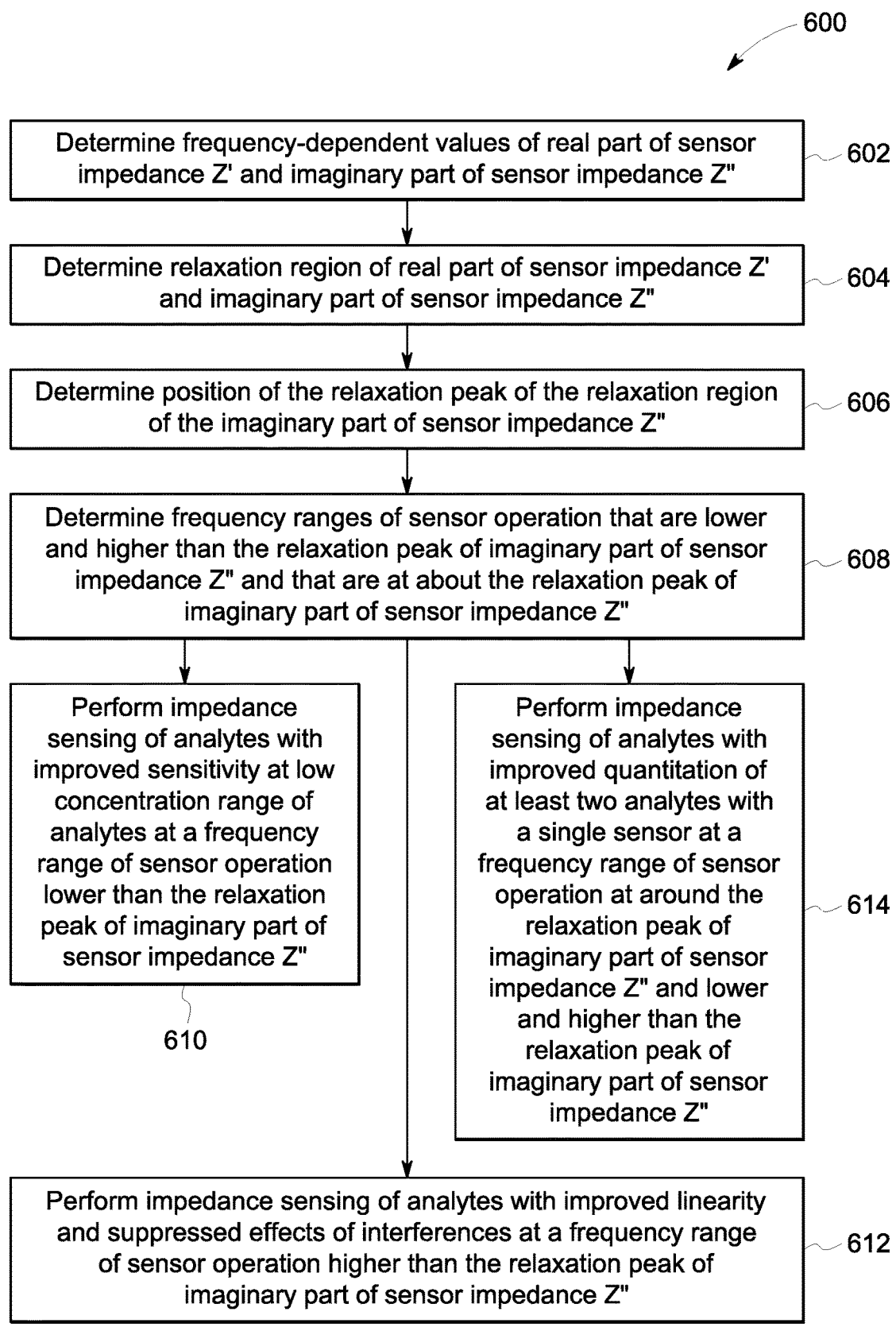
FIG. 6 illustrates a flowchart of one embodiment of a method for measuring one or more analytes of interest in a sample using an impedance gas sensor.

FIG. 6 illustrates a flowchart of one embodiment of a method 600 for measuring one or more analytes of interest in a sample using an impedance gas sensor. The method 600 can represent the operations performed by the sensing system 100 and sensor 114 described herein, or optionally can represent the operations performed by another sensing system and/or another impedance gas sensor. For example, the method 600 can represent operations performed by the system 100 and/or sensor 114 under direction of one or more software applications, or optionally can represent an algorithm useful for writing such software applications.

At 602, frequency-dependent values of a real part of sensor impedance (Z') and an imaginary part of sensor impedance (Z") are measured during exposure of the sensor to a first gas sample. In one embodiment, this gas sample is clean air, such as air that does not include an analyte of interest sought to be measured in another, different sample (e.g., methane, ethane, or another hydrocarbon). This clean air also does not include possible interference gases, such as moisture or water vapor, ozone, carbon monoxide, and other gases. The sensor 114 can apply electric current to the sensing material 308 while the sensing material 308 is exposed to (e.g., placed into contact with) the gas sample at a variety of frequencies to determine where the inflection point 410 and corresponding inflection point frequency 412 occur. The sensor 114 measures the real and imaginary parts of the impedance of the sensing material 308 during exposure to the gas sample, and these measurements are communicated to the data acquisition circuitry 116, as described herein. Optionally, the sensor 114 can only measure the imaginary parts of the impedance of the sensing material 308.

At 604, the relaxation region of the sensor impedance is determined. Sensing materials 308 of the sensor, when probed by impedance spectroscopy, exhibit a relaxation region in the impedance spectra of the sensing materials 308. Both the real part of the impedance and the imaginary part of the impedance have a relaxation region. This relaxation region can be determined by examining the real part of the measured impedance of the sensing material 308 as a function of frequency to locate where the real part of the impedance changes from high impedance value and zero slope at low frequencies to decreasing impedance values with a relatively high slope at higher frequencies and to decreasing impedance values with a relatively low slope at even higher frequencies, and where impedance values are approaching zero at the highest frequencies. Alternatively, the relaxation region can be determined by examining the imaginary part of the measured impedance of the sensing material 308 to locate where the curvature of the imaginary part of the impedance changes from a concave shape to a convex shape, or from a convex shape to a concave shape. The imaginary part of impedance exhibits a peak in negative direction that is known as a relaxation peak of the relaxation region of the imaginary part of the impedance spectrum of a sensing material 308. The frequency at which the relaxation peak of the imaginary part of the impedance spectrum reaches its negative maximum is known as characteristic relaxation frequency. This relaxation region can be alternatively determined by examining the real part 400 of the measured impedance of the sensing material 308 to locate where the slope of the real part of the impedance changes from zero slope at low frequencies to relatively high slope at higher frequencies, to relatively low slope at even higher frequencies, and again to zero slope at the highest frequencies.

At 606, a position of the relaxation peak of the relaxation region of the imaginary part of the sensor impedance is determined. This peak can be determined by identifying the inflection point frequency 412 of the sensor 114. The inflection point frequency 412 can be determined as the frequency of the electric current associated with the inflection point 410. The range 414 of different frequencies can be determined by selecting a group of frequencies that are smaller than, greater than the inflection point frequency 412 or at about the inflection point frequency 412.

At 608, frequency ranges of sensor operation are determined. These frequency ranges are lower and higher than the relaxation peak of the imaginary part of the sensor impedance and that are at or about (e.g., within 1%, within 3%, within 5%, or within 10% in different embodiments) the relaxation peak of the imaginary part of the sensor impedance. For example, the sensing material 308 of the sensor 114 can be exposed to a different, second gas sample potentially having one or more analytes of interest therein. The data acquisition circuitry 116 can communicate a control signal to the sensor 114 to direct the sensor 114 to apply electric current to the sensing material 308 via the electrodes 310, 322 only at frequencies that are greater than the inflection point frequency 412 and/or that are within the range of frequencies that are greater than the inflection point frequency 412. Operating the sensor 114 at these frequencies can improve the selective sensing of the sensor 114 (e.g., the sensitivity of the sensor 114) to one or more analytes of interest in the second sample relative to one or more other analytes (and relative to operating the sensor 114 at a frequency or frequencies that are at or below the inflection point frequency 412). The sensitivity of the sensor 114 includes a measured sensor response signal per analyte concentration unit.

Optionally, at 610, impedance sensing is performed with improved sensitivity at low concentrations of analytes as compared to traditional resistance measurements shown in FIG. 1. This sensing can be performed at a frequency range of sensor operation that is lower than the relaxation peak of the imaginary part of the sensor impedance. Optionally, at 612, impedance sensing is performed with improved linearity and suppressed effects of interferences at a frequency range of sensor operation that is higher than the relaxation peak of the imaginary part of the sensor impedance as compared to traditional resistance measurements shown in FIG. 1. Optionally, at 614, impedance sensing is performed with improved quantitation of at least two analytes with a single sensor as compared to traditional resistance measurements shown in FIG. 1. The sensing can be performed at a frequency range that is at or around the relaxation peak of the imaginary part of the sensor impedance and lower and higher than the relaxation peak of the imaginary part of the sensor impedance.

The data acquisition circuitry 116 can communicate a control signal to the sensor 114 to direct the sensor 114 to apply electric current to the sensing material 308 via the electrodes 310, 322 only at frequencies that are lower than the inflection point frequency 412 and/or that are within the range of frequencies that are lower than the inflection point frequency 412. Operating the sensor 114 at these frequencies can increase the sensitivity of sensing of the sensor 114 to one or more analytes of interest at their low concentrations relative to operating the sensor 114 at a frequency or frequencies that are at or above the inflection point frequency 412.

The data acquisition circuitry 116 can communicate a control signal to the sensor 114 to direct the sensor 114 to apply electric current to the sensing material 308 via the electrodes 310, 322 at the frequencies that are lower or greater than the inflection point frequency or at the inflection point frequency 412. Operating the sensor 114 over this relatively broad range of frequencies can provide the response pattern of sensing of multiple gases with one sensor 114. Such response pattern of sensing of multiple gases with one sensor cannot be achieved by operating only at the frequencies that are lower than the inflection point frequency, or operating only at the frequencies that are higher than the inflection point frequency, or operating only at the inflection point frequency. Such response pattern of sensing of multiple gases can be further analyzed using multivariate analysis tools or machine learning tools to accurately quantify individual gases.

Additionally, operating the sensor 114 at frequencies higher than the than the inflection point frequency can suppress the effects of interferences. For example, the sensor 114 can be less sensitive to analytes other than the analytes of interest when operating at frequencies above the inflection point frequency 412 (relative to operating the sensor 114 at a frequency or frequencies that are at or below the inflection point frequency 412). Operating the sensor 114 at these frequencies can increase the linearity of the response of the sensor 114 to the one or more analytes of interest relative to operating the sensor 114 at a frequency or frequencies that are at or below the inflection point frequency 412.

Optionally, the sensor 114 can be operated at a single frequency that is smaller or greater than the inflection point frequency 412. For example, instead of conducting the electric current to the sensing material 308 at multiple, different frequencies that are smaller than the inflection point frequency, the current can be conducted to the sensing material 308 at a single frequency that is smaller than the inflection point frequency 412. For example, instead of conducting the electric current to the sensing material 308 at multiple, different frequencies that are greater than the inflection point frequency, the current can be conducted to the sensing material 308 at a single frequency that is greater than the inflection point frequency 412. One or more analyte gases can be called as the first type of gas, while the interferences or interfering gases can be called as the second type of gas.

Figure 7:
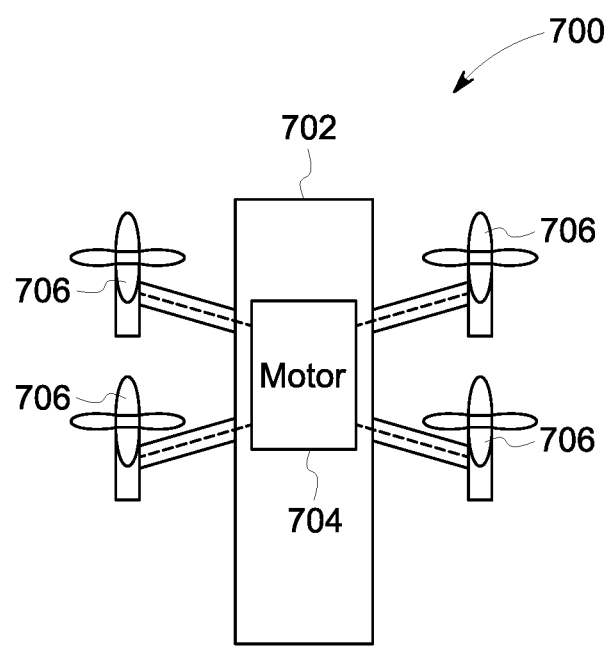
FIG. 7 illustrates a front perspective view unmanned vehicle (UMV) for determining environmental conditions according to one embodiment of the inventive subject matter described herein.

FIG. 7 illustrates an example unmanned vehicle (UMV) for determining environmental conditions. In this example, the UN/IV is a drone 700 that includes a housing 702, that houses at least one motor 704 that actuates at least one propeller 706. In the example embodiment illustrated, the drone 700 includes a single motor that is powering four separate propellers. In other example embodiments, a motor may be provided for each propeller 706. Alternatively, a single propeller may be provided. The drone 700 in one example has a width, height, and length each less than two feet in distance. In another example, the drone 700 has a width, height, and length of greater than two feet in distance. In yet another example, the one or more of the width, height, or length is less than two feet in distance while one or more of width, height, or length is greater than two feet in distance. In one example, the housing 702 is of single piece construction, while in another example, the housing is of multipiece construction.

Figure 8:
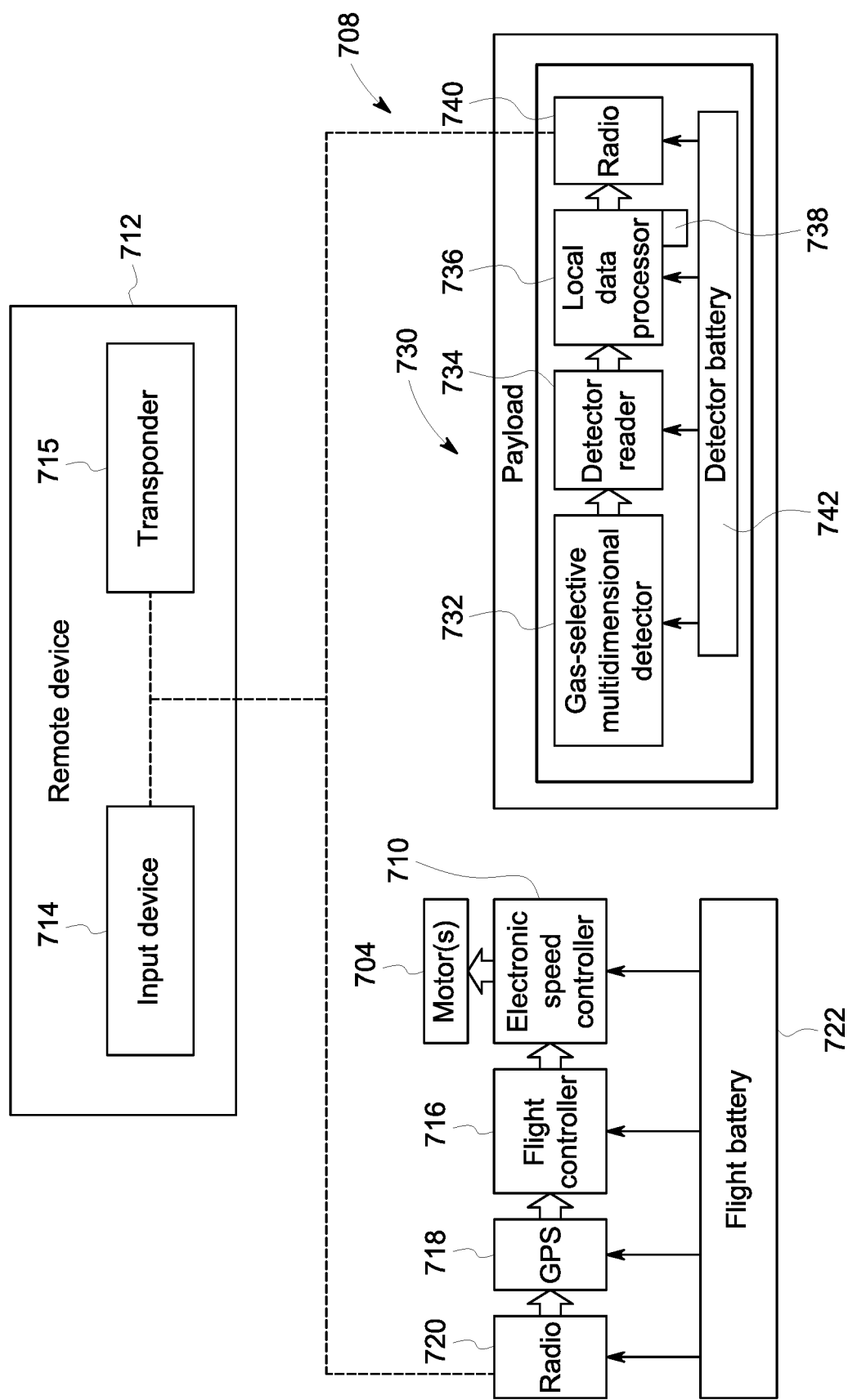
FIG. 8 illustrates a schematic block diagram of a control system for an UMV according to one embodiment of the inventive subject matter described herein.

FIG. 8 illustrates a control unit 708 of the drone 700 that is disposed within the housing 702. The control unit 708 includes an electronic speed controller 710 electrically connected to at least one motor 704 for controlling the actuation speed of at least one propeller 706. In one example, the electronic speed controller 710 includes an electronic speed controller circuit that operates to control the thrust, and revolutions per minute (RPMs) of each motor 704 for each propeller 706. The electronic speed controller 710 optionally is operable to receive operation signals from a remote device 712 to control the speed of the drone 700.

The remote device 712 may be a remote controller, wearable device including a smart watch, physiological monitoring device, or the like, portable device including a cellular telephone, iPad, iPod, or the like, or the like. Specifically, the remote device includes at least one input device 714 for controlling the speed and/or direction of the drone 700, and a transponder 715 for transmitting an operation signal to the control unit 708. The input device 714 in examples includes toggle switches, joysticks, touch screens, keyboards, keypads, compressible buttons, or the like. Optionally, instead of being controlled by a remote device 712, the drone 700 may receive inputs that provide a predetermined path of the drone 700 through an environment. In one example, the drone includes automatic flight control and collision avoidance systems that prevent the drone from colliding with objects within the environment, including stationary objects, moving objects, other drones, or the like. In one example, when the drone 700 travels a known path over numerous iterations in order to collect data, including data related to analyte gases, artificial intelligence is utilized to determine the most efficient pathway based on an initially instructed or predetermined pathway provided. In particular, the control unit 708 of the drone determines how to best moves through an environment to come the closest to staying on the predetermined pathway, while avoiding collision with other objects within the environment.

A vehicle controller 716, that in this example is a flight controller, is electrically connected to the electronic speed controller 710 and operable to control the thrust, RPMs, position, and direction of the motor 704. In particular, the vehicle controller 716 transmits signals to the electronic speed controller circuitry to provide the thrust, and RPMs of the motor 704. At least one vehicle input device 718 is electrically connected to the vehicle controller 716 to provide operation related data to the vehicle controller 716. In one example, the vehicle input device 718 is a global positioning system (GPS) that provides GPS data, including drone position data, flight path data, map data, or the like to the vehicle controller 716 for controlling the motors 704. Additionally, and alternatively, the flight input device(s) may also include internal measurement units (IMUS) utilized to measure the specific force and/or angular rate of the drone 700, gyro stabilization device(s) to provide three and/or six axis stabilization and navigation data, proximity sensors including sensors that determine the distance between the drone 700 and another object, or the like. Based on the flight data detected and measured by the vehicle input devices 718, the vehicle controller 716 is configured to facilitate movement of the drone via the vehicle controller 716 by accounting for user inputs, along with wind, position, other objects positions, or the like to ensure accuracy of the commanded flight path and to avoid collisions.

Specifically, the vehicle controller 716 determines the position of the unmanned vehicle system during a predetermined period of data acquisition. This includes drones 700 as illustrated in FIG. 7, or other unmanned vehicles, including aerial, subterranean, under-water, above-water, underground, above-ground systems, or the like. The predetermined period of data acquisition may be less than ten minutes, ten minutes, an hour, several hours, a day, or more than a day. The predetermined period of data acquisition may be the amount of time for an unmanned vehicle system to traverse a predetermined path, including the example of the drone 700, a predetermined flight path.

In one example the vehicle controller 716 dynamically controls movement of the unmanned vehicle system based on the detector signal from the detector circuit (i.e. detector circuit 240). In another example, the vehicle controller 716 dynamically controls movement based on detected route conditions signals that may be received from one or more vehicle input devices 718. These detected route condition signals include signals related to obstacles and characteristics of a pathway such as trees, buildings, other vehicles, or the like, whether conditions, including wind, rain, or the like, that cause changes in a vehicle path to avoid collision, or to avoid a slow-down. In yet another example, the vehicle controller 716 is configured to dynamically control movement of the unmanned vehicle system by dynamically controlling movement based on instructions received in the vehicle controller 716, including a predetermined flight path stored in a memory. Similarly, historical data in a memory may be used to dynamically control the movement of the unmanned vehicle system. In yet another example, the vehicle controller 716 dynamically controls movement of the unmanned vehicle system based on more than one signal received, including in one example a detected route condition signal and detector signals from the detector circuit. In each example of dynamic control, the vehicle controller autonomously makes determinations related to the movement of the unmanned vehicle system based on inputs and signals received within the unmanned vehicle system. Alternatively, the vehicle controller 716 is configured to prevent movement during the predetermined period. Specifically, the unmanned vehicle system remains approximately stationary for the predetermined period of data acquisition. In yet another alternative embodiment, the unmanned vehicle system moves and is controlled by operation signals of a remote input device 712.

A transponder 720 is also electrically connected to the vehicle input devices 718, vehicle controller 716, and electronic speed controller 710 for communicating information to and from the control system 708 including data from and related to the vehicle input devices 718, a remote input device 712, other transponders including the analyte sensor transponder 740, or the like. In one example, the transponder is a radio. In yet another example, the transponder includes a receiving device and a transmitting device for receiving and transmitting signals that include data, including navigation data, speed data, directional data, acceleration data, motor related data, analyte related data, communications, command signals, or the like.

A vehicle battery 722 is electrically coupled to at least one of a motor 704, electronic speed controller 710, vehicle controller 716, vehicle input device 718, or transponder 720. The vehicle battery 722 may be coupled to each of these devices, or may include a plurality of batteries each coupled to a device individually where the plurality of batteries together from the vehicle battery 722.

Getting sensor based systems onto the drone often can prove difficult because of the relative size of the drone compared to the sensor based system. In particular, the payload, or amount of weight that a drone is able to carry at any given time is equal to the motor thrust times the number of motors times the hover throttle percent, less the weight of the drone. Specifically, the greater the power-to-weight ratio a drone has, the greater the payload the drone may carry. In one example, the weight of the drone includes the weight of the housing 702, motors 704, propellers 706, electronic speed controller 710, vehicle controller 716, vehicle input device 718, the transponder 720, and vehicle battery 722. Therefore, the sensor system must be light weight and of size and shape to be housed by the drone 700 while not exceeding the available payload of the drone 700

To this end, the drone 700 also includes an environmental sensor system 730 that may be any of the sensors or sensor systems described in detail herein including the sensor system 100 of FIG. 1. In this example, the sensor system 730 includes a sensing element 732 that in one example is the sensing element 114 of FIG. 1. Specifically, the sensing element 732 may detect characteristics or properties of fluid (including gases and liquids) via a resonant or non-resonant impedance spectral response. One or more of inductor-capacitor-resistor resonant circuits (LCR resonators) may measure the resonant impedance spectral response. A non-resonant impedance spectral response is measured when the circuit does not contain an inductor. The resonant or non-resonant impedance spectrum of the sensing element 732 in proximity to the sample varies based on sample composition and/or components. The measured resonant or non-resonant impedance values Z' (which may be the real part of resonant impedance, Zre) and Z" (which may be the imaginary part of resonant impedance, Zim) reflect the response of the sensing element 732 to the fluid. Based on the detected signals from the sensor system 730, the vehicle controller 716 may store the detected signals, including environmental data within historical data of a memory during a predetermined period of data acquisition. This historical data may then be used by the vehicle controller to control the operation and movement of the unmanned vehicle system. Additionally, the historical data saved in the memory may be transmitted to a remote device for review, including a remote device at a control center, a remote device that transmits operation signals, a remote device that does not transmit operation signals, or the like. Alternatively, the historical data received during the predetermined period of data acquisition may be displayed on an input device 714 such as a touch screen, or output device, such as a display screen of the unmanned vehicle system.

Other embodiments of the inventive subject matter described herein include other designs of sensors besides resonant and non-resonant impedance sensors. Other sensors can be capacitor sensors, electro-mechanical resonator sensors (e.g., tuning forks, cantilever sensors, acoustic device sensors), thermal sensors, optical sensors, acoustic sensors, photoacoustic sensors, near-infrared sensors, ultraviolet sensors, infrared sensors, visible light sensors, fiber-optic sensors, reflection sensors, multivariable sensors, or single-output sensors. The sensor may generate electrical or optical output responses upon exposure to a measured sample.

An electrical field may be applied to the sensing material or film of the sensing element 732 via electrodes. The distance between the electrodes, may define the magnitude of the electric field applied to the sensing element 732 (e.g., to the sensing material or film). The electrodes may be in direct contact with the sensing material. For example, the sensing element 732 may be a combination of a sensing region and associated circuits and/or the sensing region may be coated with the sensing material. The sensing material may be semiconductor material or metal oxide material.

Data from the sensing element 732 may be acquired via data acquisition circuitry 734, which may be optionally associated with data processing circuitry 736, where additional processing and analysis may be performed. In one example, the data acquisition circuitry 734 merely acquires reading from the sensing element 732 and records these reading with a database, or memory 738. This recorded data may then be transmitted as a detector signal to a remote processing device (not shown) that includes processing circuitry for analysis. The recorded data may be transmitted as a detector signal by a sensor transponder 740 that is electrically connected to the memory 738 and data acquisition circuitry 734. As a result, the sensor transponder 740 may transmit the detector signal in real-time to the remote processing device, may transmit detector signal at or after a predetermined time, or may transmit the detector signal when prompted by a signal transmitted by the remote device. In one example the remote device is the remote device 712.

In yet another example, the vehicle controller 716 receives the detector signal and operates the drone to change a route to fly to where more analyte is being detected. Alternatively, a preset course is provided to the vehicle controller 716, including but not limited to X directions, Y directions, Z directions, straight paths, curved paths, or the like. In another example, a vehicle controller 716 is provided with an initial path that is executed until the detector signal detects a gas of interest, then, based on the detector signal, the vehicle controller autonomously maps out the area affected by the analyte. In example embodiment the map includes 3-dimensional mapping, mapping of analyte in an area, including based on wind patterns. In yet another example multiple drones simultaneously supply detector signals that includes detector data to a system processor, or remote process and based on this combined detector data an analyte surface map is formed. In this manner a team of UMV could enter an area, including a battlefield with toxic gas, an area with a dangerous gas leak, or the like to map out exact dangerous locations to provide to soldiers, first responders, or the like.

In examples, any and all transmissions may include one or more wireless or wired components, and the sensor transponder 740 may also communicate with the other components of the system drone 700 including the transponder 720. Suitable communication models include wireless or wired. At least one suitable wireless model includes radio frequency devices, such as radio frequency identification (RFID) wireless communications. Other wireless communication modalities may be used based on application specific parameters. For example, where there may be electromagnetic field (EMF) interference, certain modalities may work where others may not. The data acquisition circuitry 734 optionally can be disposed within the sensing element 732. In yet another example, a secondary storage device (not shown) is inserted into the sensor system 730 and acquisition data or analysis is transmitted through a port to the secondary storage device.

The data acquisition circuitry 734 may be in the form of a sensor reader, and may be a battery-operated device and/or may be powered using energy available from the main control system or by using harvesting of energy from ambient sources (light, vibration, heat, or electromagnetic energy). Additionally, the data acquisition circuitry 734 may receive data from one or more sensing elements 732. The sensors system 730 may be placed on an exterior surface of the housing 702 of the drone or within the housing 702 of the drone 700 in a position to be exposed to fluid within an environment. In this manner the drone may be used for monitoring of unauthorized activities such as burning waste without permit, smoking in unapproved areas, chemical processing of raw ingredients to produce illegal substances, and other unauthorized activities. Similarly, methane gas may be detected in an area, indicating an unsafe environment. The drone 700 may be used in industrial, urban, residential, public, medical, military facilities and other facilities outdoors or indoors for gas monitoring. The data acquisition circuitry 734 may include one or more processors for analyzing the data received from the sensing element 732. For example, the one or more processors may be one or more computer processors, controllers (e.g., microcontrollers), or other logic-based devices that perform operations based on one or more sets of instructions (e.g., software). The instructions on which the one or more processors operate may be stored on a tangible and non-transitory computer readable storage medium, such as a memory device. The memory device may include a hard drive, a flash drive, RAM, ROM, EEPROM, and/or the like. Alternatively, one or more of the sets of instructions that direct operations of the one or more processors may be hard-wired into the logic of the one or more processors, such as by being hard-wired logic formed and/or stored in the hardware of the one or more processors.

Optionally, a sensing battery 742 may be electrically connected to at least one of the sensing element 732, data acquisition circuitry 734, data processing circuitry 736, and/or sensor transponder 740 to power each. In other example embodiments, at least one of, if not all of the sensing element 732, data acquisition circuitry 734, data processing circuitry 736, and/or sensor transponder 740 are powered by the vehicle battery 722. The sensing battery 742 may be on battery or include a plurality of batteries connected to one another for powering the components of the environmental sensor system 730. The sensing battery 742 may be removable, rechargeable, and replaceable, supplemented through alternative power sources such as solar power, or the like.

By utilizing the sensing material described herein in association with the sensing elements 732, data acquisition circuitry 734, data processing circuitry 736, transponder 740, and/or sensing battery 742 has a weight that is less than the payload weight of the drone 700. In one example, the environmental sensor system 730 has a total weight in a range between 5 g and 1 kg. In another example, the total weight of the environmental sensor system 730 is 500 g. In this manner, an environmental sensor system 730 that has detection and sensing capabilities far greater than other sensing devices such has infrared cameras, videos, smoke detection devices and the like is provided. Specifically, the environmental sensor 730 is able to distinguish between an analyte and other fluids, or gases, including relative humidity to detect the presence of the analyte. Consequently, sensing capabilities are enhanced.

In one example, the environmental sensor 730 is a gas-selective multidimensional detector, where the detector includes a material that is predictably affected by the environment and that is positioned onto a substrate and is probed with an integrated circuit analyzer at multiple electrical frequencies. In another embodiment, the gas-selective multidimensional detector is an electrical resonator that has multiple outputs and measurements that detect changes in the resonant properties. In particular, in example embodiments, each embodiment of a sensor system as described in relation to any and all of the FIGS. provided herein is provided.

In yet another example the environmental sensor system 730 includes a gas-selective multidimensional detector that may be a non-resonant or resonant device. Both types of devices utilize metal oxide semiconducting sensing elements. To bring the sensing selectivity to non-resonant devices, impedance readout was performed across the dielectric relaxation region of the impedance response of the sensor element. Such readout provides performance enhancement attributes of the metal oxide sensor element over its traditional classic resistance readout. These performance enhancements include the enhancement of response sensitivity at low concentrations of analyte, the enhancement of linearity of the response to analyte and the enhancement of sensitivity at high concentrations of analyte. Further, selection of the proper excitation conditions of the sensor may control the type of power law coefficients of the analyte response and interference responses, and rejection of interferences. The application of the resonant response mechanisms in the detector performance further improves rejection of interferences.

Therefore, in one embodiment, the UMV may be an above-ground vehicle travelling at different speeds and heights above ground. The UMV may have the ability to fly outdoors and indoors. The UMV may have the ability to fly outdoors and indoors with a flight path that is conformal to the objects on the surface. The UMV may have the ability to fly outdoors and indoors at distances down to about 1 cm from the objects on the surface. The UMV maybe have flying speed down to zero such as performing hovering above a certain area. The UMV may have the ability to fly into and out from the areas such as outdoor areas and confined indoor or outdoor areas that may have dangerous conditions to humans for them to enter for area inspection. Nonlimiting examples of such conditions include volatiles and particulates in the ambient air produced from drug manufacturing, volatiles from manufacturing of improvised explosive devices, and other harmful conditions. The UMV may be flying at different heights above the surfaces. The UMV may be able to fly-in into local areas of relatively high concentrations of volatiles, for example directly above different closed or open containers. The UMV may be able to fly near surfaces and to lift-off the particulates from the surfaces for their essentially real-time analysis.

In all, the detection capabilities that are brought about by the multivariable sensors described in this invention may be comparable with the capabilities of the traditional analytical equipment such as gas chromatography systems, laser spectroscopy systems, mas-spectrometry systems and other systems. However, these and other traditional analytical systems are often are desktop units or field units, requiring a significant power to operate (at least 10,000 mW and more) and have relatively large size of at least 10 cm×10 cm×10 cm and larger. These and other features of traditional analytical systems make them difficult to implement on UMVs to fly conformal to the relatively objects on the surfaces with object sized of only several millimeters or less. However, the sensor system of this invention may be light weight and of size and shape to be easily housed by the UMV for such tasks.

Figure 9:
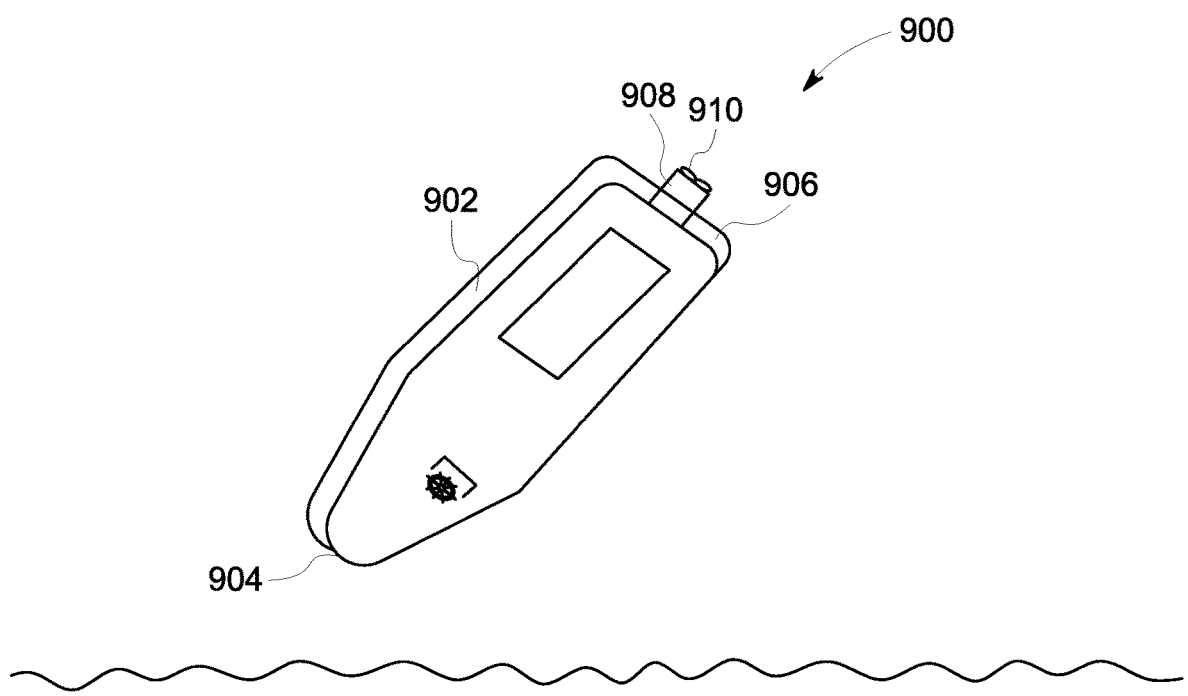
FIG. 9 illustrates a front perspective view unmanned vehicle (UMV) for determining environmental conditions according to one embodiment of the inventive subject matter described herein.

FIG. 9 illustrates another example unmanned vehicle (UMV) for determining environmental conditions. In this example, the UMV is a remote controlled aquatic vehicle 900 that includes a housing 902 extends from a front 904, or bow, to a back 906, or stern. While in this example the aquatic vehicle is illustrated as operating on the water, in other example embodiment the aquatic vehicle may be submerged and operate under the water. An example of this type of embodiment includes a remote controlled mini-submarine. In this example embodiment, secured to the back 906 of the aquatic vehicle 900 is a motor 908 that includes a propeller 910. In one example the propeller 910 is pivotably secured to the housing and configured to pivot side to side to control the direction of the aquatic vehicle 900. In another example the housing includes a rudder to control the direction of the aquatic vehicle. The propeller 910 may rotate clockwise and/or counterclockwise to control the whether the boat move forward or backwards. In one example the aquatic vehicle has a width, height, and length of greater than two feet in distance. In yet another example, the one or more of the width, height, or length is less than two feet in distance while one or more of width, height, or length is greater than two feet in distance. In one example, the housing 902 is of single piece construction, while in other example, the housing is of multipiece construction.

Figure 10:
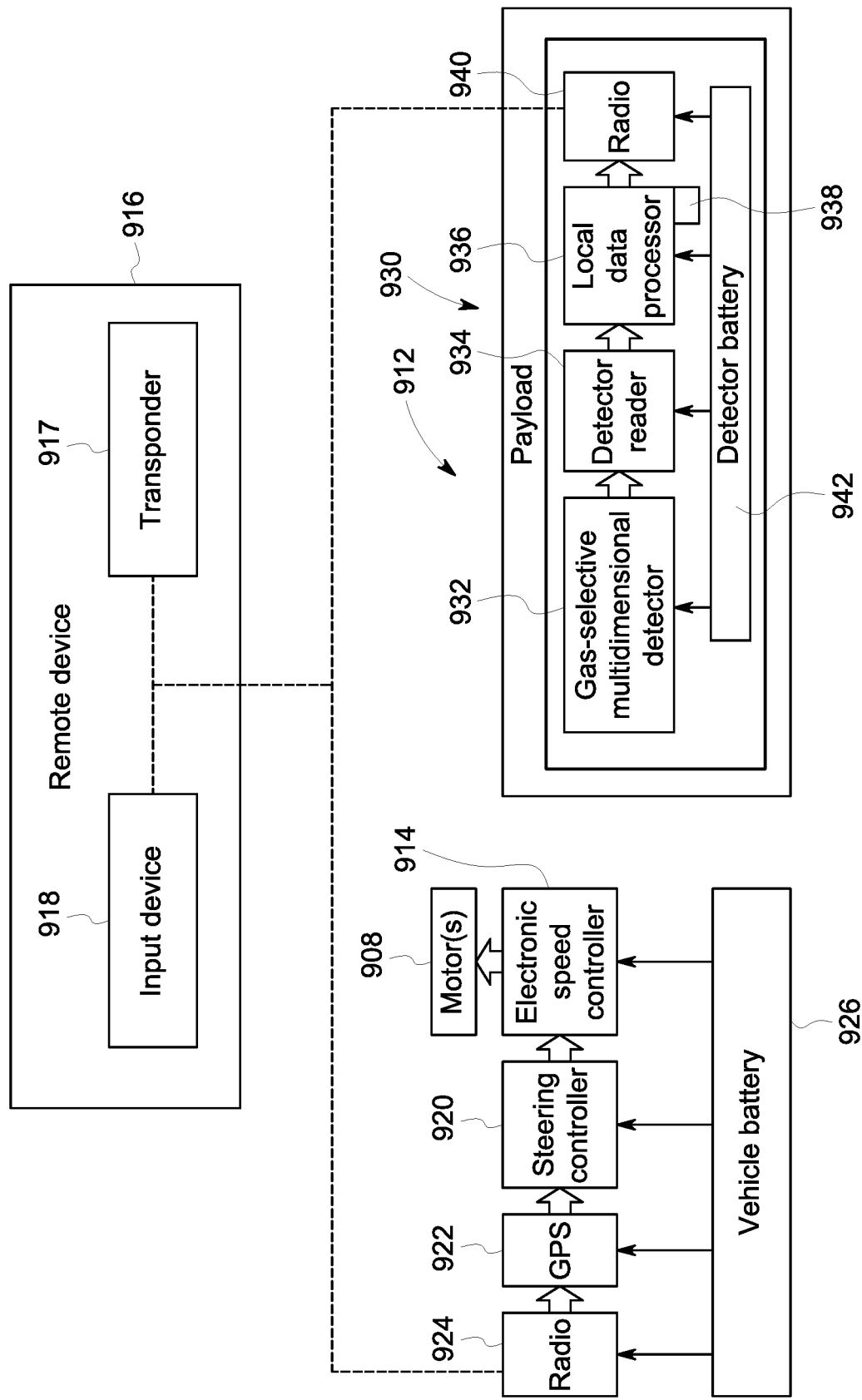
FIG. 10 illustrates a schematic block diagram of a control system for an UMV according to one embodiment of the inventive subject matter described herein.

FIG. 10 illustrates a control unit 912 of the aquatic vehicle 900 that is disposed within the housing 902. The control unit 912 includes an electronic speed controller 914 electrically connected to the motor 908 for controlling the actuation speed of the propeller 910. In one example, the electronic speed controller 914 includes an electronic speed controller circuit that operates to control the rotational speed of the propeller 910. The electronic speed controller 914 optionally is operable to receive signals from a remote device 916 to control the speed of the aquatic vehicle 900. The remote device 916 may be a remote controller, wearable device including a smart watch, physiological monitoring device, or the like, portable device including a cellular telephone, iPad, iPod, or the like, or the like. Specifically, the remote device includes at least one vehicle input device 918 for controlling the speed and/or direction of the aquatic vehicle 900, and a transponder 917 for transmitting an operation signal to the control unit 912. The vehicle input device 918 in examples includes toggle switches, joysticks, touch screens, keyboards, keypads, compressible buttons, or the like. Optionally, instead of being controlled by a remote device 916, the aquatic vehicle 900 may receive inputs that provide a predetermined path of the aquatic vehicle 900 through an environment. In one example, when the aquatic vehicle 900 travels a known path over numerous iterations in order to collect data, including data related to analyte gases, artificial intelligence is utilized to determine the most efficient pathway based on an initially instructed or predetermined pathway provided. In particular, the control unit 912 of the aquatic vehicle 900 determines how to best move through an environment to come the closest to staying on the predetermined pathway, while avoiding collision with other objects within the environment.

A vehicle controller that is a steering controller 920 is electrically connected to the electronic speed controller 914 and direction of the aquatic vehicle 900. In one example, the steering controller operates the position of the motor 908 and propeller 910 by pivoting the motor 908 left or right. At least one position input device 922 is electrically connected to the steering controller 920. In one example, the position input device 922 is a global positioning system (GPS) that provide GPS data, including aquatic vehicle position data, map data, or the like to the steering controller 920 for controlling the position of the motor 908 and propeller 910. Based on the position data detected and measured by the position input devices 922, the steering controller 920 is configured to facilitate movement of the aquatic vehicle 900 via the steering controller 920 by accounting for user inputs, along with currents, position, other objects positions, or the like to ensure accuracy of the commanded path.

Similar to the control unit 708 of the drone 700, the control unit 912 also includes a transponder 924 and aquatic vehicle battery 926. These operate and function in a similar manner as previously described.

The remote aquatic vehicle 900 also includes an environmental sensor system 930 that may be another of the sensors or sensor systems described in detail herein including the sensor system 100 of FIG. 1. In this example, the sensor system 930 includes a sensing element 932 that in one example is the sensing element 114 of FIG. 1. Specifically, the sensing element 932 may detect characteristics or properties of fluid (including gases and liquids) via a resonant or non-resonant impedance spectral response. One or more of inductor-capacitor-resistor resonant circuits (LCR resonators) may measure the resonant impedance spectral response. A non-resonant impedance spectral response is measured when the circuit does not contain an inductor. The resonant or non-resonant impedance spectrum of the sensing element 932 in proximity to the sample varies based on sample composition and/or components. The measured resonant or non-resonant impedance values Z' (which may be the real part of resonant impedance, Zre) and Z" (which may be the imaginary part of resonant impedance, Zim) reflect the response of the sensing element 932 to the fluid.

An electrical field may be applied to the sensing material or film of the sensing element 932 via electrodes. The distance between the electrodes, may define the magnitude of the electric field applied to the sensing element 932 (e.g., to the sensing material or film). The electrodes may be in direct contact with the sensing material. For example, the sensing element 932 may be a combination of a sensing region and associated circuits and/or the sensing region may be coated with the sensing material. The sensing material may be semiconductor material or metal oxide material.

The sensor system 930 may also include data acquisition circuitry 934, data processing circuitry 936, memory 938, sensor transponder 940, and sensing battery 942. These may operate and function in manners as described in relation to the sensor system 730 of drone 700 in order to detect analyte fluids or gases.

Figure 11:
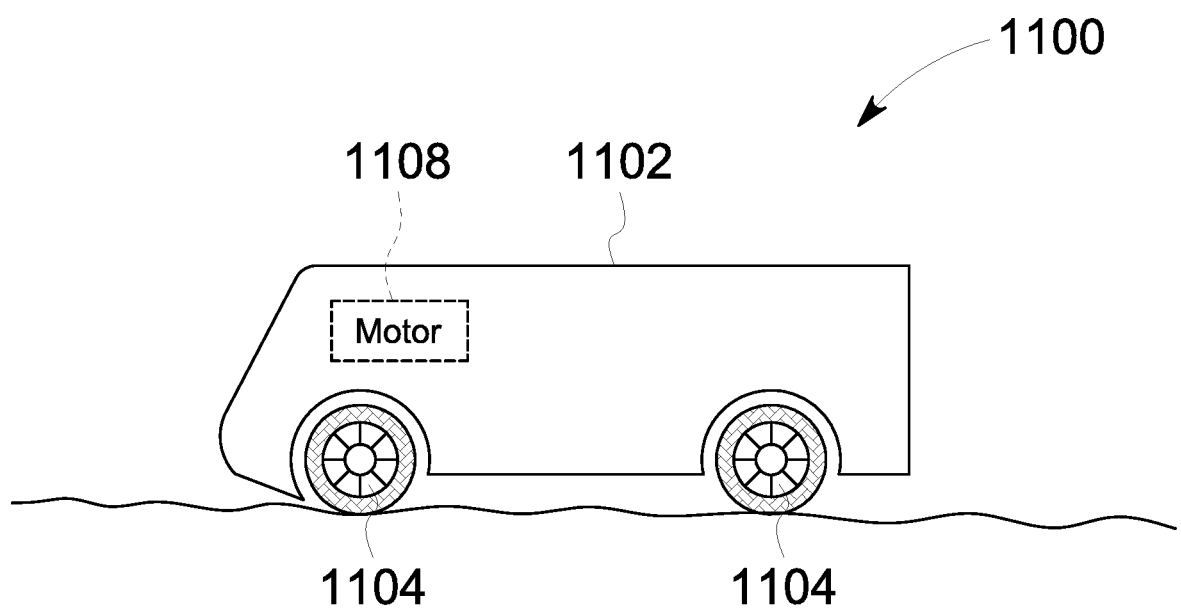
FIG. 11 illustrates a front perspective view unmanned vehicle (UMV) for determining environmental conditions according to one embodiment of the inventive subject matter described herein.

FIG. 11 illustrates yet another example unmanned vehicle (UMV) for determining environmental conditions. In this example, the UMV is a remote controlled land vehicle 1100 that includes a body 1102 that may be considered a housing, that includes at least one wheel 1104. While in this example the UMV is a land vehicle that traverse on top of the earth, in other example embodiments the land vehicle traverses underground, or into the side of a mountain, hill, or the like. In one such example embodiment the land vehicle is a mining vehicle that tunnels into the earth, mountain, hill, or the like. In one example the body 1102 includes four wheels 1104 received by a chassis that provide steering control of the wheels 1104. The land vehicle 1100 also includes a motor 1108 that propels the wheels 1104. In one example the land vehicle 1100 has a width, height, and length of greater than two feet in distance. In yet another example, the one or more of the width, height, or length is less than two feet in distance while one or more of width, height, or length is greater than two feet in distance. In one example, the body 1102 is of single piece construction, while in other example, the body, or housing, is of multipiece construction.

Figure 12:
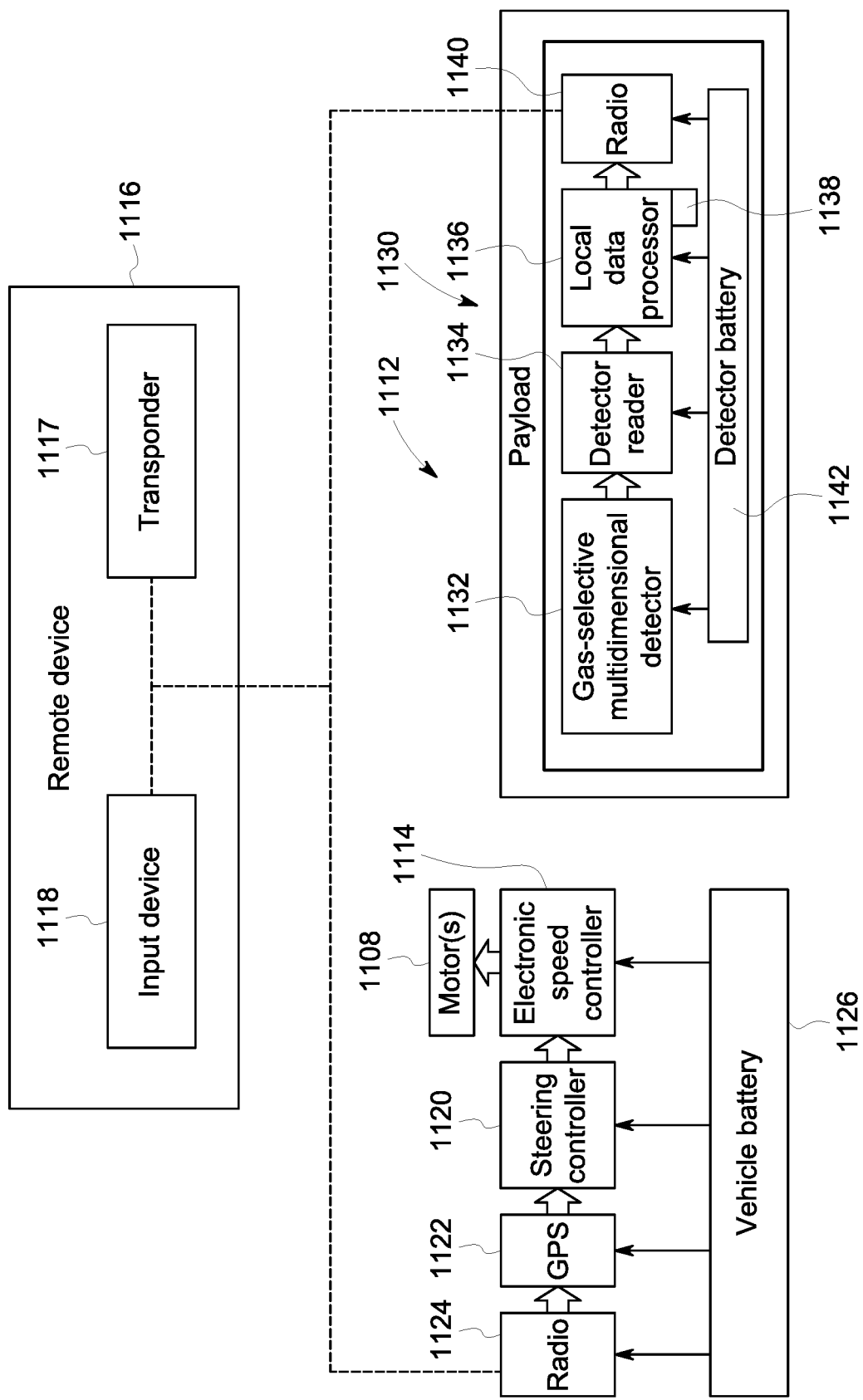
FIG. 12 illustrates a schematic block diagram of a control system for an UMV according to one embodiment of the inventive subject matter described herein.

FIG. 12 illustrates a control unit 1112 of the land vehicle 1100 that is disposed within the body 1102. The control unit 1112 includes an electronic speed controller 1114 electrically connected to the motor 1108 for controlling the actuation speed for propelling the wheels 1104. In one example, the electronic speed controller 1114 includes an electronic speed controller circuit that operates to control the rotational speed of the wheels 1104. The electronic speed controller 1114 optionally is operable to receive signals from a remote device 1116 to control the speed of the land vehicle 1100. The remote device 1116 may be a remote controller, wearable device including a smart watch, physiological monitoring device, or the like, portable device including a cellular telephone, iPad, iPod, or the like, or the like. Specifically, the remote device 1116 includes at least one vehicle input device 1118 for controlling the speed and/or direction of the land vehicle 1100, and a transponder 1117 for transmitting an operation signal to the control unit 1112. The vehicle input device 1118 in examples includes toggle switches, joysticks, touch screens, keyboards, keypads, compressible buttons, or the like. Optionally, instead of being controlled by a remote device 1116, the land vehicle 1100 may receive inputs that provide a predetermined path of the land vehicle 1100 through an environment. In one example, when the land vehicle 1100 travels a known path over numerous iterations in order to collect data, including data related to analyte gases, artificial intelligence is utilized to determine the most efficient pathway based on an initially instructed or predetermined pathway provided. In particular, the control unit 1112 of the land vehicle 1100 determines how to best move through an environment to come the closest to staying on the predetermined pathway, while avoiding collision with other objects within the environment.

A vehicle controller that is a steering controller 1120 is electrically connected to the electronic speed controller 1114 and direction of the land vehicle 1100. In one example, the steering controller operates the position of the wheels 1104. At least one position input device 1122 is electrically connected to the steering controller 1120. In one example, the position input device 1122 is a global positioning system (GPS) that provide GPS data, including land vehicle position data, map data, or the like to the steering controller 1120 for controlling the position of the wheels 1104. Based on the position data detected and measured by the position input devices 1122, the steering controller 1120 is configured to facilitate movement of the land vehicle 1100 via the steering controller 1120 by accounting for user inputs, pathway, position, other objects positions, or the like to ensure accuracy of the commanded path.

Similar to the control unit 708 of the drone 700, the control unit 1112 also includes a transponder 1124 and vehicle battery 1126. These operate and function in a similar manner as previously described.

The remote land vehicle 1100 also includes an environmental sensor system 1130 that may be another of the sensors or sensor systems described in detail herein including the sensor system 100 of FIG. 1. In this example, the environmental sensor system 1130 includes a sensing element 1132 that in one example is the sensing element 114 of FIG. 1. Specifically, the sensing element 1132 may detect characteristics or properties of fluid (including gases and liquids) via a resonant or non-resonant impedance spectral response. One or more of inductor-capacitor-resistor resonant circuits (LCR resonators) may measure the resonant impedance spectral response. A non-resonant impedance spectral response is measured when the circuit does not contain an inductor. The resonant or non-resonant impedance spectrum of the sensing element 1132 in proximity to the sample varies based on sample composition and/or components. The measured resonant or non-resonant impedance values Z' (which may be the real part of resonant impedance, Zre) and Z" (which may be the imaginary part of resonant impedance, Zim) reflect the response of the sensing element 1132 to the fluid.

An electrical field may be applied to the sensing material or film of the sensing element 1132 via electrodes. The distance between the electrodes, may define the magnitude of the electric field applied to the sensing element 1132 (e.g., to the sensing material or film). The electrodes may be in direct contact with the sensing material. For example, the sensing element 1132 may be a combination of a sensing region and associated circuits and/or the sensing region may be coated with the sensing material. The sensing material may be semiconductor material or metal oxide material.

The sensor system 1130 may also include data acquisition circuitry 1134, data processing circuitry 1136, memory 1138, sensor transponder 1140, and sensing battery 1142. These may operate and function in manners as described in relation to the sensor system 730 of drone 700 in order to detect analyte fluids or gases.

In all, FIGS. 7, 9, and 11 illustrate example UMVs 700, 900, 1100. Still, these are each only examples of UMVs that may include the sensor systems described herein. Other example UMVs include underwater UMVs, underground UMVs, or the like. Specifically, the sensor systems each utilize an impedance response as described herein. Each UMV also includes a sensor system described herein and a remote control that allows an operator to remotely operate the UMV to make determinations related to analyte gases in an environment.

Figure 13:
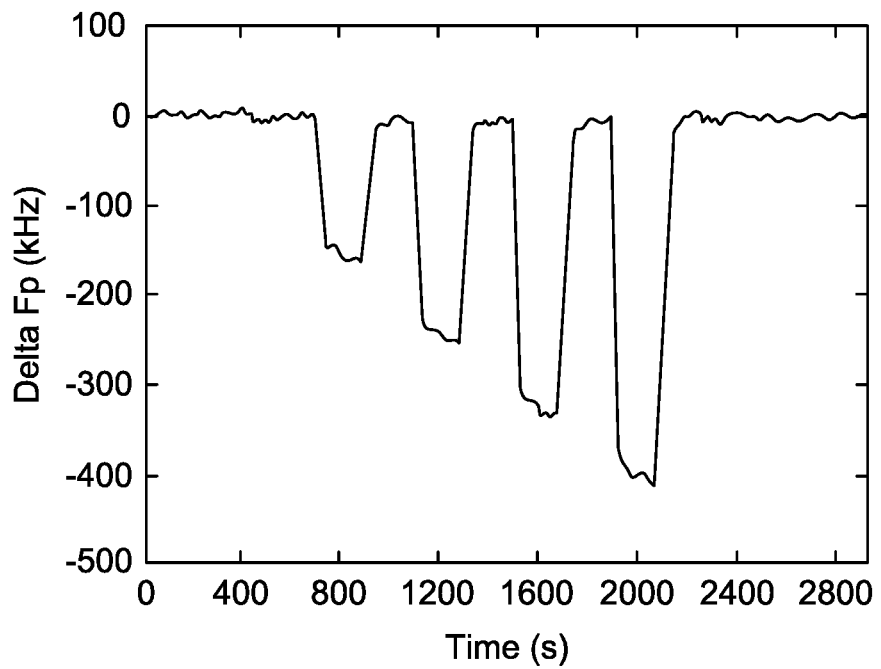
FIG. 13 illustrates a graph of measurements of frequency of different concentrations of methane using an autonomous sensor node according to one embodiment of the inventive subject matter described herein.
Figure 14:
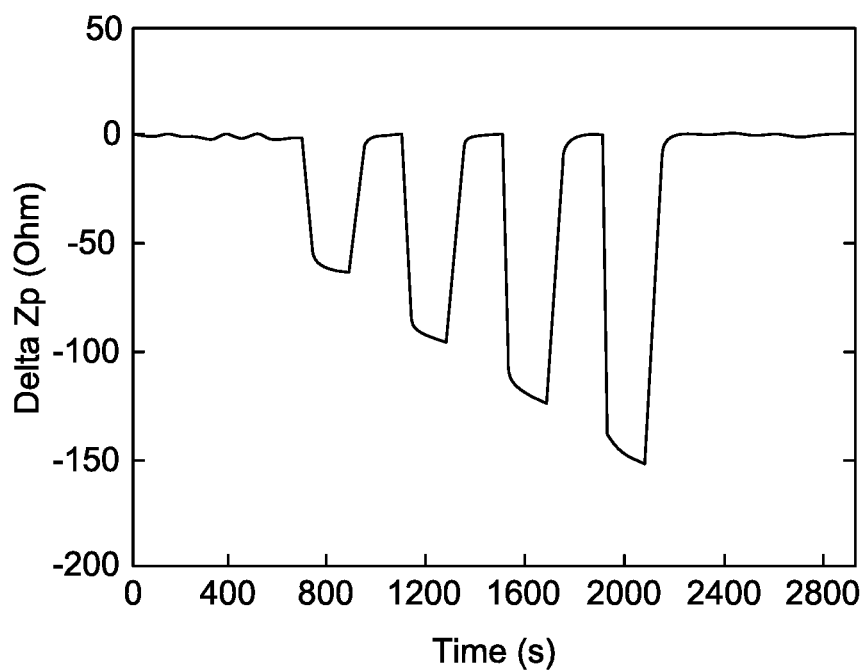
FIG. 14 illustrates a graph of measurements of resistance of different concentrations of methane using an autonomous sensor node according to one embodiment of the inventive subject matter described herein.

In one example, the environmental sensor system includes an autonomous sensor node for measurements of explosive gases such as methane. An example of measurements of different concentrations of methane using the developed autonomous sensor node is presented in FIGS. 13-14. The environmental sensor system 730 of this example was exposed to increasing concentrations of methane of 0.22, 0.44, 0.67, and 0.89% and predictably changed its Fp (FIG. 13) and Zp (FIG. 14) responses as a function of methane concentration.

Figure 15A:
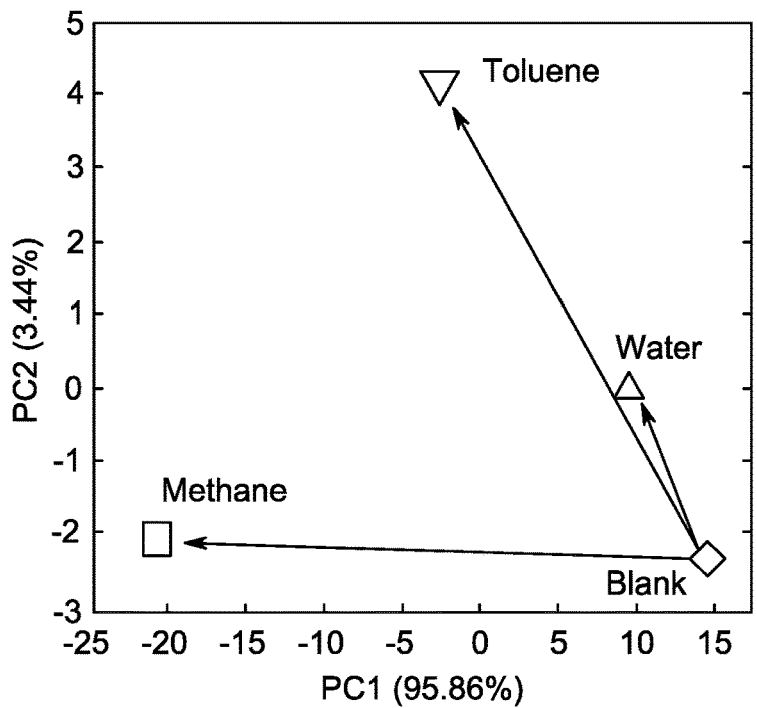
FIG. 15A illustrates a graph of an example response of an environmental sensor system that utilizes an impedance response to determine the presence of an analyte according to one embodiment of the inventive subject matter described herein.
Figure 15B:
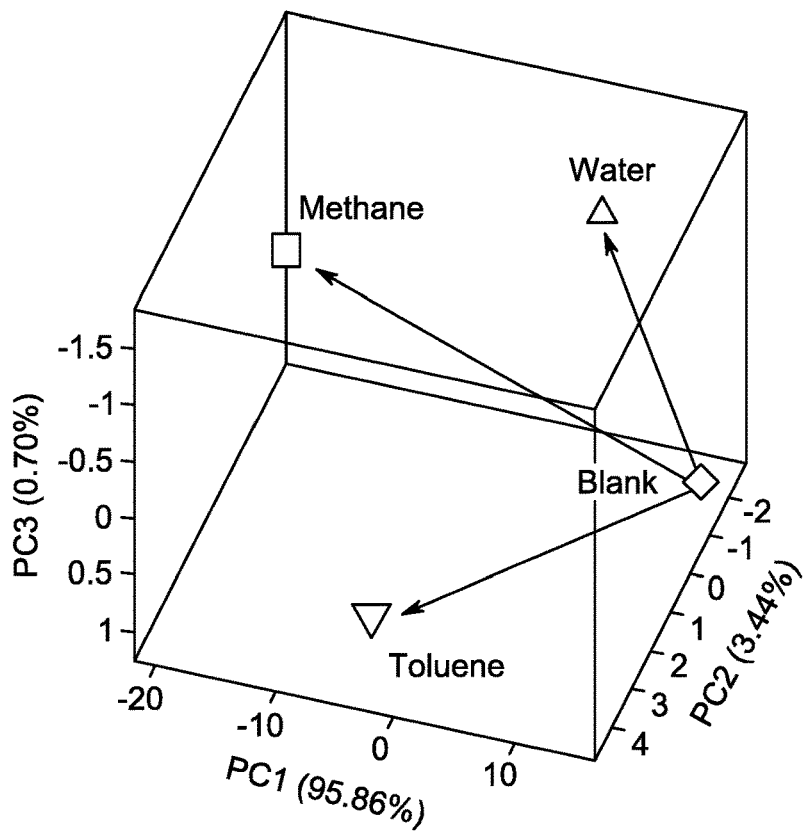
FIG. 15B illustrates a graph of an example response of an environmental sensor system that utilizes an impedance response to determine the presence of an analyte according to one embodiment of the inventive subject matter described herein.

The autonomous sensor node was exposed to methane and to high concentrations of water vapor and toluene vapor as interferences. In this test, methane concentration was 0.89%, water vapor concentration was ~70% relative humidity and toluene vapor concentration was ~70% of its saturated vapor pressure. Results of these measurements after applying our multivariable statistical methodology to reject interferences are presented in FIGS. 15A and 15B. FIGS. 15A and 15B illustrate a discrimination between methane analyte and interferences (water and toluene vapors) using the autonomous sensor node and applied principal components analysis. Scores plots of (FIG. 15A) PC1 vs PC2 and (FIG. 15B) PC1 vs PC2 vs PC3. Methane concentration was 0.89%, water vapor concentration was ~70% relative humidity and toluene vapor concentration was ~70% of its saturated vapor pressure.

In an example, the methane sensor element may be configured to operate in the resonant mode. In an experiment, such a resonant sensor was exposed to methane at concentrations of 1.1, 2.2, 3.3, 4.4, 5.5 and 6.6% in air. A total of 18 sets of methane exposures were produced over 8.6 hours of testing. Each set of methane exposures contained six methane concentrations of 1.1, 2.2, 3.3, 4.4, 5.5 and 6.6%. Each methane concertation was presented to the sensor for 100 seconds followed by a 100 second exposure of the sensor to the blank carrier gas. The time between the sets of methane exposures was 500 seconds. Data acquisition for the sensor was 10 seconds between saved data points resulting in 3096 data points over the time of 8.6-h test.

Figure 16:
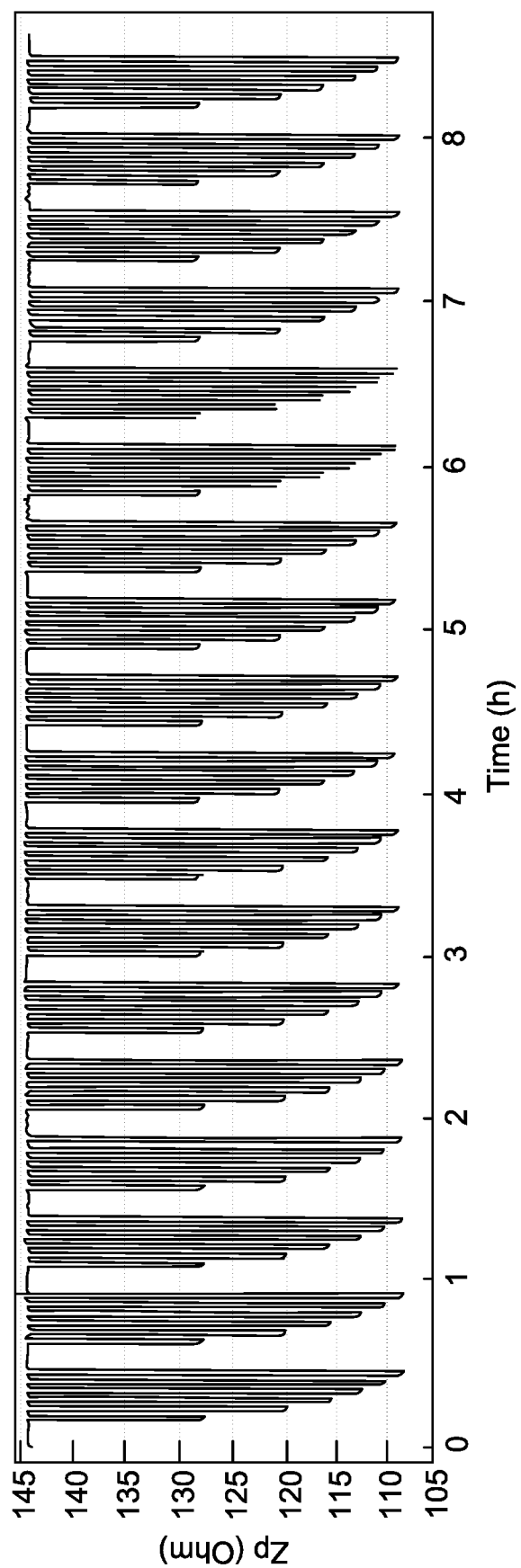
FIG. 16 illustrates a graph of raw impedance data over time according to one embodiment of the inventive subject matter described herein.

FIG. 16 illustrates an exemplary raw Zp data from the sensor for more than eight hours of operation demonstrating highly reproducible sensor response and stable baseline.

The steady state regions of the sensor response to methane and air from only one set of methane exposures were then utilized to build a transfer function between sensor response and methane concentrations. Three data points from each region from one set of methane exposures were used for the transfer function development, resulting in 21 data points for transfer function (18 data points from exposures to six methane concentrations and three data points from exposure to the blank). The transfer function was built in a Design for Six Sigma Process Tool (DFSS Process Tool) developed at GE Global Research. The developed transfer function was further applied in the DFSS Process Tool to the whole raw data of 3096 data points.

Figure 17:
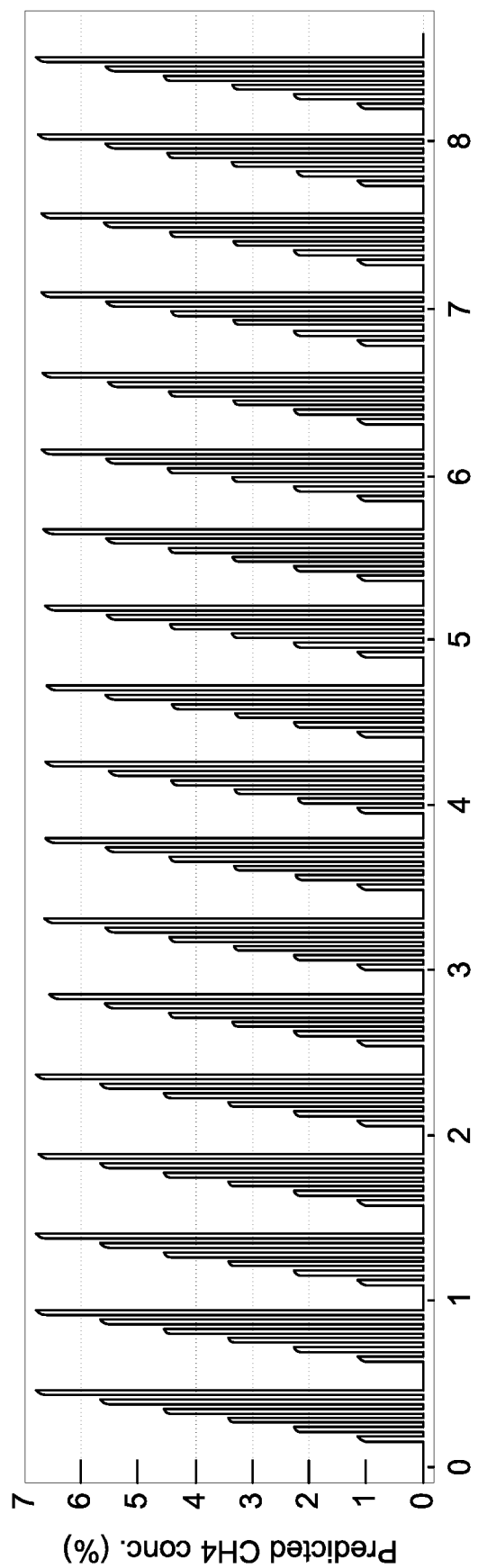
FIG. 17 illustrates a graph of sensor data after application of a transfer function according to one embodiment of the inventive subject matter described herein.

FIG. 17 illustrates sensor data after application of the developed transfer function with the predicted concentrations of methane as the Y axis of the sensor response.

In an example, to evaluate the quality of predictions of methane concentrations with the resonant sensor, comparison between predicted and actual values of methane concentrations was further performed. This comparison was done when the sensor reached state-state responses upon exposures to methane or after each recovery with the blank carrier gas. The predicted values of methane concentrations were extracted from all eighteen sets of methane exposures. Each set of methane exposures had 21 extracted points. An additional three points of sensor response after the last methane exposure were also included. Thus, the total number of predicted values of methane state-state values for comparison with actual methane concentrations was 381 points (18 sets×21 points per set+3 points at the end of test).

The absolute error of prediction of methane concentrations $\sigma_{ABS}$ was calculated as the difference between the actual $[CH_4]_{ACT}$ and predicted $[CH_4]_{PRED}$ methane concentrations:

$$\sigma_{ABS}=[CH_4]_{ACT}-[CH_4]_{PRED}$$

Further, the relative error of predicted methane concentrations $\sigma_{REL}$ was calculated as the absolute error of the prediction of methane concentrations $\sigma_{ABS}$ over the actual methane concentrations $[CH_4]_{ACT}$ and expressed as percent error:

$$\sigma_{REL}=100\%\sigma_{ABS}/[CH_4]_{ACT}$$

Figure 18A:
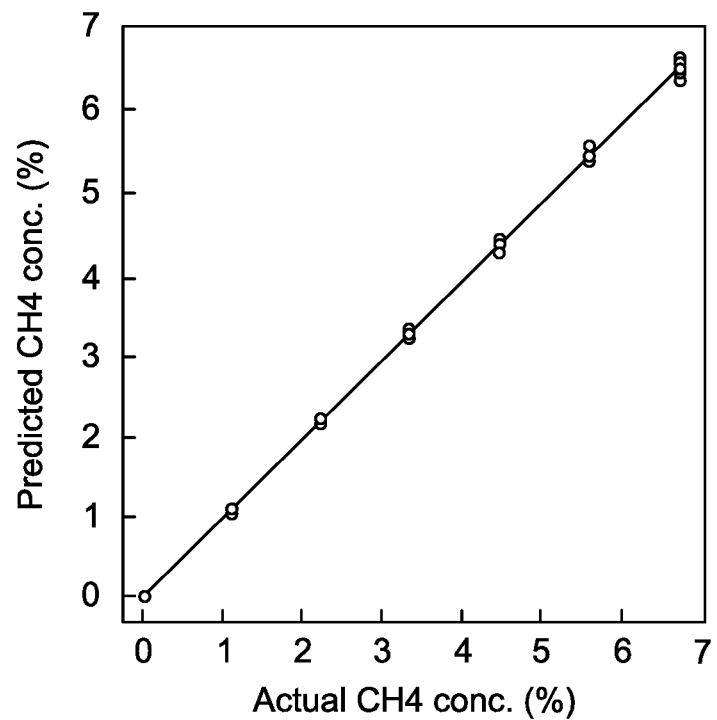
FIG. 18A illustrates a graph of a plot between actual and predicted concentrations of methane according to one embodiment of the inventive subject matter described herein.
Figure 18B:
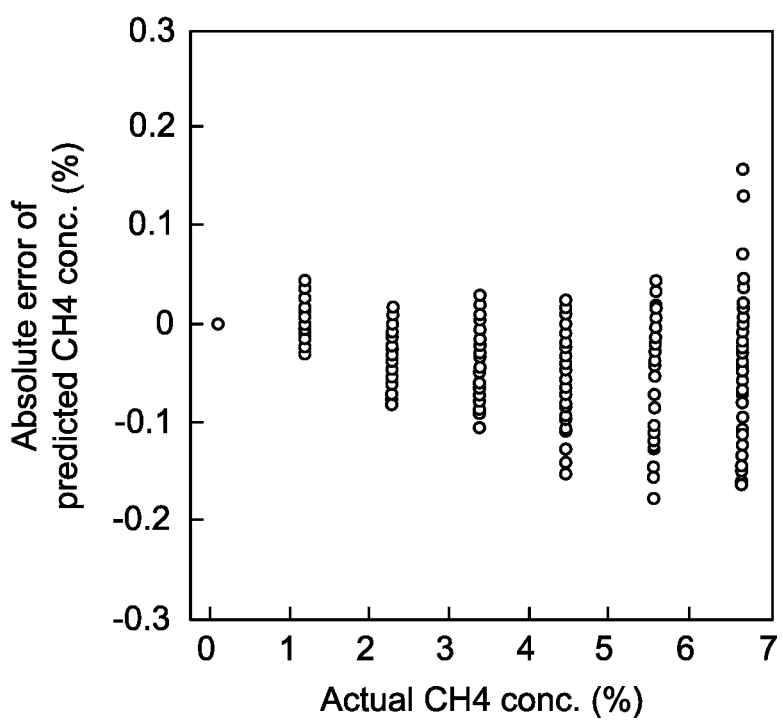
FIG. 18B illustrates a graph of absolute error of prediction for methane concentrations as a function of actual method concentrations according to one embodiment of the inventive subject matter described herein.
Figure 18C:
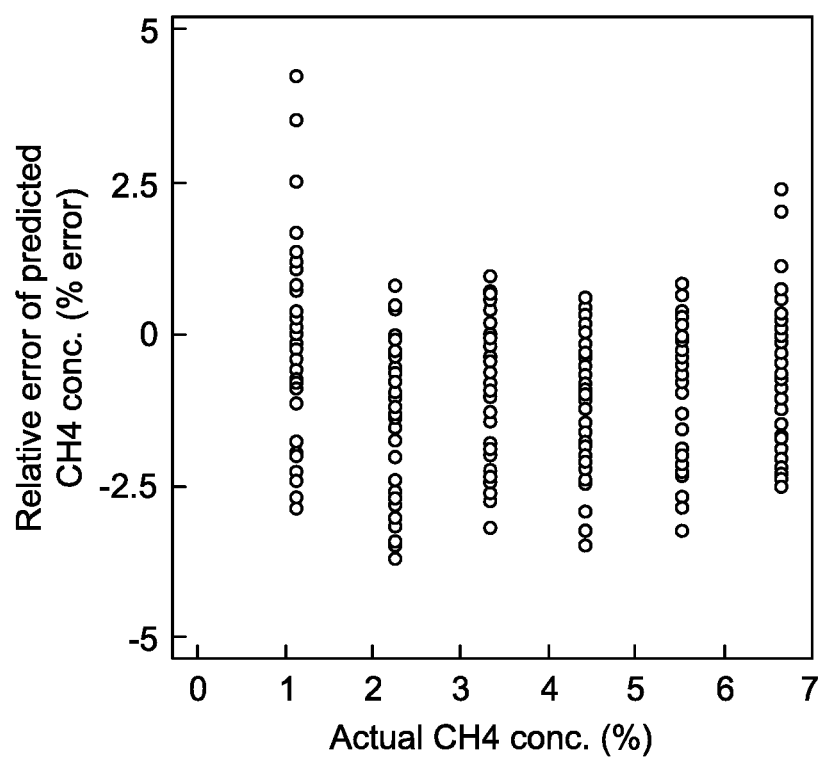
FIG. 18C illustrates a graph of relative error of prediction of methane concentrations plotted as a function of actual method concentration according to one embodiment of the inventive subject matter described herein.

The correlation plot between the actual and predicted concentrations of methane is illustrated in FIG. 18A. This plot depicts all 381 points that were used for this correlation. The absolute error of prediction of methane concentrations $\sigma_{ABS}$ (units of methane %) is plotted as a function of actual methane concentrations in FIG. 18B. The relative error of prediction of methane concentrations $\sigma_{REL}$ (units of % of error, not methane %) is plotted as a function of actual methane concentrations in FIG. 18C. Such data presentation depicted in FIG. 18A-C demonstrates that the developed sensor operated reliably and with the relative error of only less than 5% over the 8.6 h of test. Such error should be acceptable for the further implementation of this sensor design in a wireless sensor node.

Figure 19:
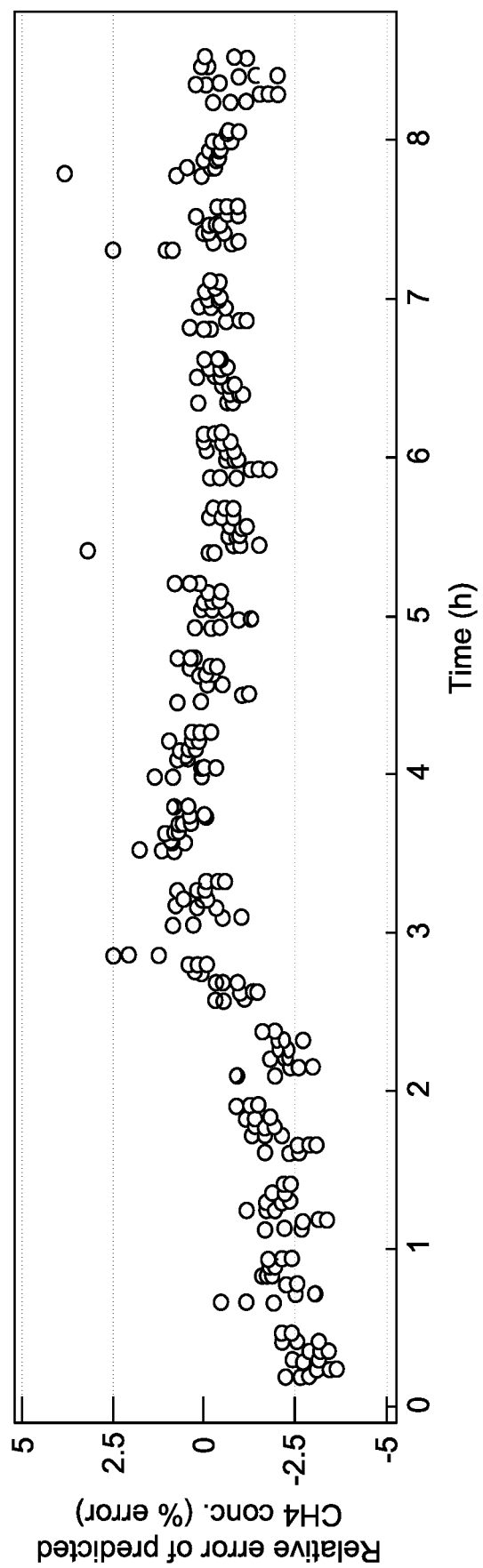
FIG. 19 illustrates a graph of relative error of predicted method plotted as a function of time according to one embodiment of the inventive subject matter described herein.

The relative error of predicted methane concentrations $\sigma_{REL}$ is plotted as a function of 8.6 h of the test in FIG. 19. Such data presentation demonstrates that the sensor did not degrade its prediction ability over the test period. Tests performed with methane concentration of up to 6.6% demonstrated that the developed sensor operated with relative error of <5% over 8.6 h of test.

Figure 20:
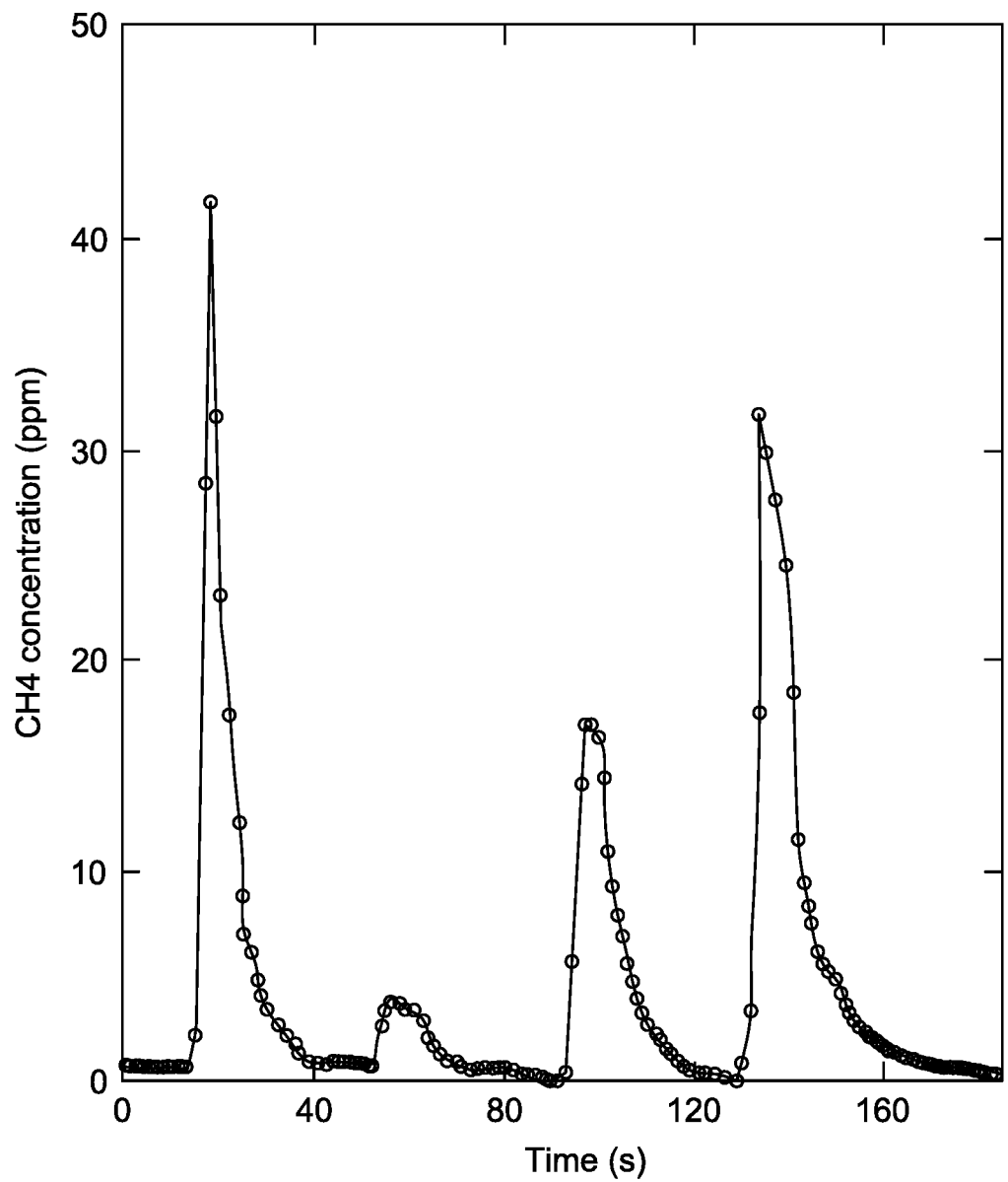
FIG. 20 illustrates a graph of real-time detection of methane leak from a tank according to one embodiment of the inventive subject matter described herein.

In one example, an experiment was provided with the sensor node as described above that was positioned onto a drone and tested for its detection of methane during operation of the drone. A tank with 100% of methane was positioned outdoors in the open area to release small amounts of methane into ambient air. The UAV with the attached sensor node was flying in a circular point of interest (POI) pattern at 0.8 meter/sec around the methane gas tank detecting the methane leak in real time. Results of the real-time detection of methane leak from the tank utilizing a drone similar to the drone 700 of FIG. 7 are depicted in FIG. 20. This periodic pattern of methane response is the result of flying of the UAV with the attached sensor node in a circular pattern around the methane gas tank detecting the methane leak in real time. The different concentrations of the detected methane is the result of the random wind pattern during the experiment.

Thus provided are numerous embodiments of UMV for determining environmental conditions. By utilizing an environmental sensor system that uses an impedance readout of a sensing element performed across the dielectric relaxation region of the impedance response of the sensor element, the accuracy of the environmental sensor system is greatly enhanced, while greatly reducing the payload of the environmental sensor system compared to other environmental sensor systems that provide a similar accuracy to the environmental sensor system described herein. Because the payload is greatly reduced, the environmental sensor system may be coupled to UMVs, including drone, aquatic vehicles on the water and under the water, land vehicles on land and underground, and the like to detect analytes in a given environment. By using the environmental sensor system on the UMV, potentially dangerous and harmful analytes, such as methane, may be detected remotely, without endangering the user. The user may remotely control the UMV, or the UMV may operate based on sensor data related to the environment in order to detect the analyte of interest, enhancing detection of hazardous gases, fluids, and the like. This increases user safety while improving on environmental detection.

In one or more embodiment, an unmanned vehicle system is provided that includes a housing, and an environmental sensor system coupled to the housing, the environmental sensor system configured to detect one or more environmental conditions of an environment in operational contact with the electronic device. The environmental sensor includes a sensing element that includes a sensing material and electrodes configured to apply electrical stimuli to the sensing material at different frequencies, and a detector circuit configured to detect and quantify at least one analyte gas by measuring impedance of the sensing element at one or more frequencies of the different frequencies during exposure of the sensing material to the at least one analyte gas. The detector circuit is configured to control one or more of a low detection range of the sensing material to at least one analyte gas, a high detection range of the sensing material to the at least one analyte gas, a response linearity of the sensing material to the at least one analyte gas, a dynamic range of measurements of the at least one analyte gas by the sensing material, or a rejection of one or more interfering gases by the sensing material. The unmanned vehicle system also includes a control unit comprising one or more processors communicatively coupled with the environmental sensor, the one or more processors are configured to receive a detector signal from the detector circuit of the environmental sensor indicative of the one or more environmental conditions, and control the movement of the unmanned vehicle system based on an operation signal of a remote device, instructions received at a vehicle controller, the detector signal, or in response to detected route conditions.

Optionally, the one or more processors are configured to determine the at least one analyte gas based on the detector signal from the detector circuit of the environmental sensor. Alternatively, the vehicle system also includes an output device in communication with the one or more processors and configured to display notifications related to the at least one analyte gas determined.

Optionally, the one or more processors are configured to transmit the detector signal from the detector circuit of the environmental sensor to the remote device.

Optionally, the remote device is a wearable electronic device. In one aspect, the wearable electronic device is at least one of a smart watch or physiological monitoring device.

Optionally, the control unit comprises a memory configured to store the detector signal from the detector circuit of the environmental sensor indicative of the one or more environmental conditions. In another aspect, the housing includes at least one propeller.

Optionally, the unmanned vehicle system is one of a drone, remote controlled vehicle, remote controlled vessel, or remote controlled aircraft. In another aspect, the one or more environmental conditions include one or more of at least one particle matter contaminants, ultraviolet radiation exposure, ambient temperature, ambient atmospheric pressure, ambient relative humidity, or environmental sensor system acceleration.

Optionally the environmental sensor system has a weight in a range between 0.005 grams and 1 gram. In another aspect, the housing includes at least one motor within the housing for powering the unmanned vehicle system, and a vehicle battery electrically coupled to the at least one motor. Alternatively, the environmental sensor is within the housing and electrically coupled to the vehicle battery. In one aspect, the environmental sensor is within the housing and includes a detector battery electrically coupled to the detector circuit separate from the vehicle battery. In another aspect, a flight controller electrically coupled to the at least one motor, a global positioning system electrically coupled to the flight controller, and an electronic speed controller electrically coupled to the at least one motor.

In one or more other embodiments, an unmanned vehicle system for determining environmental conditions is provided that includes a housing including at least one propeller, at least one motor for driving a propeller, and a vehicle controller electrically coupled to the at least one motor and configured to receive command signals from a remote device to control the operation of the at least one motor and direction of the unmanned vehicle system. An environmental sensor system is coupled to the housing and includes a sensing element that includes a sensing material and electrodes configured to apply electrical stimuli to the sensing material at different frequencies, and a detector circuit configured to detect and quantify at least one analyte gas by measuring impedance of the sensing element at one or more frequencies of the different frequencies during exposure of the sensing material to the at least one analyte gas. The detector circuit is configured to control one or more of a low detection range of the sensing material to at least one analyte gas, a high detection range of the sensing material to the at least one analyte gas, a response linearity of the sensing material to the at least one analyte gas, a dynamic range of measurements of the at least one analyte gas by the sensing material, or a rejection of one or more interfering gases by the sensing material. A control unit is coupled to the environmental sensor and includes one or more processors communicatively coupled with the environmental sensor and the vehicle controller. The one or more processors are configured to receive an environmental signal from the detector circuit of the environmental sensor system indicative of the at least one analyte gas.

Optionally, the environmental sensor system has a weight in a range between 0.005 grams and 1 gram. In another aspect the vehicle system also includes a vehicle battery electrically coupled to the at least one motor.

Optionally, the environmental sensor system includes a detector battery electrically coupled to the detector circuit separate from the vehicle battery. In another aspect, the vehicle system also includes a global positioning system electrically coupled to the vehicle controller, and an electronic speed controller electrically coupled to the at least one motor.

In one or more embodiments, a method of collecting environmental conditions is provided that includes positioning a vehicle including an environmental sensor system to detect an environmental condition, and applying electrical stimuli at different frequencies with the environmental sensor system, the environmental sensor system comprising a sensing element that includes a sensing material and electrodes. A detector circuit measures impedance of the sensing element at one or more frequencies of the different frequencies during exposure of the sensing material to at least one analyte gas, wherein the detector circuit is configured to detect and quantify the at least one analyte gas. The method also includes controlling one or more of a low detection range of the sensing material to the at least one analyte gas, the high detection range of the sensing material to the at least one analyte gas, a response linearity of the sensing material to the at least one analyte gas, a dynamic range of measurements of the at least one analyte gas by the sensing material, or a rejection of one or more interfering gases by the sensing material with the detector circuit.

Optionally, positioning the vehicle includes flying the vehicle to a predetermined position. Alternatively, positioning the vehicle includes pivoting a propeller of an aquatic vehicle. In another aspect, positioning the vehicle includes steering the unmanned vehicle based on an operation signal received by a control unit coupled to the unmanned vehicle. Optionally, the unmanned vehicle is a remote controlled vehicle. In another aspect, positioning the vehicle includes steering the unmanned vehicle based on a detector signal received from the detector circuit.

In one or more embodiments, an unmanned vehicle system that includes an environmental sensor system configured to detect one or more environmental conditions of an environment in operational contact with the unmanned vehicle system. The environmental sensor system includes a sensing element that includes a sensing material and electrodes configured to apply electrical stimuli to the sensing material at different frequencies, and a detector circuit configured to detect and quantify at least one analyte gas by measuring impedance of the sensing element at one or more frequencies of the different frequencies during exposure of the sensing material to the at least one analyte gas. The detector circuit is configured to control one or more of a low detection range of the sensing material to at least one analyte gas, a high detection range of the sensing material to the at least one analyte gas, a response linearity of the sensing material to the at least one analyte gas, a dynamic range of measurements of the at least one analyte gas by the sensing material, or a rejection of one or more interfering gases by the sensing material. The unmanned vehicle system also includes one or more processors are configured to receive a detector signal from the detector circuit of the environmental sensor indicative of the one or more environmental conditions, and position the unmanned vehicle system during a predetermined period of data acquisition.

Optionally, to position the unmanned vehicle system during the predetermined period of data acquisition the one or more processors are configured to dynamically control movement based on the detector signal from the detector circuit. Alternatively, to position the unmanned vehicle system during the predetermined period of data acquisition the one or more processors are configured to dynamically control movement based on detected route condition signals. In yet another aspect, to position the unmanned vehicle system during the predetermined period of data acquisition the one or more processors are configured to dynamically control movement based on instructions received in a vehicle controller including a predetermined flight path. Optionally, to position the unmanned vehicle system during the predetermined period of data acquisition the one or more processors are configured to dynamically control movement based on detected route condition signals and the detector signal from the detector circuit.

In another aspect, to position the unmanned vehicle system during the predetermined period of data acquisition the one or more processors are configured to prevent movement during the predetermined period. Alternatively, to position the unmanned vehicle system during the predetermined period of data acquisition the one or more processors are configured to dynamically control movement based on operation signals of a remote device. In another aspect, to position the unmanned vehicle system during the predetermined period of data acquisition the one or more processors are configured to dynamically control movement based on historical data stored in a memory.

Optionally, the one or more processors are configured to store the environmental data of the detector signal in the historical data of the memory during the predetermined period of data acquisition. In another aspect, the one or more processors are configured to transmit the environmental data of the detector signal in the historical data to a remote device. Alternatively, the one or more processors are configured to display the environmental data of the detector signal in the historical data.

As used herein, an element or step recited in the singular and proceeded with the word "a" or "an" should be understood as not excluding plural of said elements or steps, unless such exclusion is explicitly stated. Furthermore, references to "one embodiment" of the presently described inventive subject matter are not intended to be interpreted as excluding the existence of additional embodiments that also incorporate the recited features. Moreover, unless explicitly stated to the contrary, embodiments "comprising," "including," or "having" (or like terms) an element, which has a particular property or a plurality of elements with a particular property, may include additional such elements that do not have the particular property.

As used herein, terms such as "system" or "controller" may include hardware and/or software that operate(s) to perform one or more functions. For example, a system or controller may include a computer processor or other logic-based device that performs operations based on instructions stored on a tangible and non-transitory computer readable storage medium, such as a computer memory. Alternatively, a system or controller may include a hard-wired device that performs operations based on hard-wired logic of the device. The systems and controllers shown in the figures may represent the hardware that operates based on software or hardwired instructions, the software that directs hardware to perform the operations, or a combination thereof.

As used herein, terms such as "operably connected," "operatively connected," "operably coupled," "operatively coupled" and the like indicate that two or more components are connected in a manner that enables or allows at least one of the components to carry out a designated function. For example, when two or more components are operably connected, one or more connections (electrical and/or wireless connections) may exist that allow the components to communicate with each other, that allow one component to control another component, that allow each component to control the other component, and/or that enable at least one of the components to operate in a designated manner.

It is to be understood that the subject matter described herein is not limited in its application to the details of construction and the arrangement of elements set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the presently described subject matter without departing from its scope. While the dimensions, types of materials and coatings described herein are intended to define the parameters of the disclosed subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

What is claimed is:

1. An unmanned vehicle system comprising:
    an environmental sensor system coupled to a housing and configured to detect one or more environmental conditions of an environment in operational contact with the unmanned vehicle system, the environmental sensor system comprising a non-resonant sensor that includes:
        a sensing element that includes a sensing material and electrodes configured to apply electrical stimuli to the sensing material at multiple frequency ranges; and
        a detector circuit configured to detect and quantify at least one analyte gas by measuring one or more impedance responses of the sensing element at one or more frequencies of the multiple frequency ranges during exposure of the sensing material to the at least one analyte gas, wherein the detector circuit comprises one or more passive electrical components configured to be electrically coupled to the sensing element,
        wherein the detector circuit is configured to electrically couple the one or more passive electrical components to the sensing element, electrically decouple the one or more passive electrical components from the sensing element, or both, to control the one or more frequencies of the one or more impedance responses of the sensing element corresponding to one or more of a low detection range of the sensing material to the at least one analyte gas, a high detection range of the sensing material to the at least one analyte gas, an impedance response linearity of the sensing material to the at least one analyte gas, a dynamic range of measurements of the at least one analyte gas by the sensing material, or a rejection of one or more interfering gases by the sensing material; and
    one or more processors are configured to:
        receive a detector signal from the detector circuit of the environmental sensor system indicative of the one or more environmental conditions; and
        control movement of the unmanned vehicle system based on an operation signal of a remote device, instructions received at a vehicle controller, the detector signal, or in response to detected route conditions.

2. The unmanned vehicle system of claim 1, wherein the one or more processors are configured to determine the at least one analyte gas based on the detector signal from the detector circuit of the environmental sensor system.

3. The unmanned vehicle system of claim 1, wherein the one or more processors are configured to transmit the detector signal from the detector circuit of the environmental sensor system to the remote device.

4. The unmanned vehicle system of claim 1, wherein the remote device is a wearable electronic device.

5. The unmanned vehicle system of claim 4, wherein the wearable electronic device is at least one of a smart watch or physiological monitoring device.

6. The unmanned vehicle system of claim 1, wherein the vehicle controller comprises a memory configured to store the detector signal from the detector circuit of the environmental sensor system indicative of the one or more environmental conditions.

7. The unmanned vehicle system of claim 1, wherein the housing includes at least one propeller.

8. The unmanned vehicle system of claim 1, wherein the unmanned vehicle system is one of aerial, subterranean, under-water, above-water, under-ground, or above ground system.

9. The unmanned vehicle system of claim 1, wherein the one or more environmental conditions include one or more of at least one gas pollutants, multiple gases pollutants, volatiles, volatiles from drug manufacturing, volatiles from manufacturing of improvised explosive devices, particle matter contaminants, ultraviolet radiation exposure, ambient temperature, ambient atmospheric pressure, ambient relative humidity, or environmental sensor system acceleration.

10. The unmanned vehicle system of claim 1, wherein the environmental sensor system has a weight in a range between 0.005 grams and 1 gram.

11. The unmanned vehicle system of claim 1, wherein the housing includes at least one motor within the housing for powering the unmanned vehicle system, and a vehicle battery electrically coupled to the at least one motor.

12. The unmanned vehicle system of claim 11, wherein the environmental sensor system is within the housing and electrically coupled to the vehicle battery.

13. The unmanned vehicle system of claim 11, wherein the environmental sensor system is within the housing and includes a detector battery electrically coupled to the detector circuit separate from the vehicle battery.

14. The unmanned vehicle system of claim 11, further comprising a flight controller electrically coupled to the at least one motor, a global positioning system electrically coupled to the flight controller, and an electronic speed controller electrically coupled to the at least one motor.

15. The unmanned vehicle system of claim 1, wherein the unmanned vehicle system performs at least one of gas leaks surveillance, gas pollution surveillance, industrial monitoring, environmental monitoring, urban monitoring, traffic pollution monitoring, homeland security monitoring, military monitoring, or search and rescue monitoring.

16. The unmanned vehicle system of claim 1, wherein the one or more passive electrical components comprise respective switches that electrically couple the one or more passive electrical components to the sensing element, electrically decouple the one or more passive electrical components from the sensing element, or both.

17. An unmanned vehicle system for determining environmental conditions comprising:
a housing including at least one propeller;
at least one motor for driving a propeller;
a vehicle controller electrically coupled to the at least one motor and configured to receive command signals from a remote device to control operation of the at least one motor and direction of the unmanned vehicle system;
an environmental sensor system comprising a non-resonant sensor that includes:
a sensing element that includes a sensing material and electrodes configured to apply electrical stimuli to the sensing material at multiple frequency ranges; and
a detector circuit configured to detect and quantify at least one analyte gas by measuring one or more impedance responses of the sensing element at one or more frequencies of the multiple frequency ranges during exposure of the sensing material to the at least one analyte gas, wherein the detector circuit comprises one or more passive electrical components configured to be electrically coupled to the sensing element,
wherein the detector circuit is configured to electrically couple the one or more passive electrical components to the sensing element, electrically decouple the one or more passive electrical components from the sensing element, or both, to control the one or more frequencies of the one or more impedance responses of the sensing element corresponding to one or more of a low detection range of the sensing material to the at least one analyte gas, a high detection range of the sensing material to the at least one analyte gas, an impedance response linearity of the sensing material to the at least one analyte gas, a dynamic range of measurements of the at least one analyte gas by the sensing material, or a rejection of one or more interfering gases by the sensing material; and
a control unit comprising one or more processors communicatively coupled with the environmental sensor system and the vehicle controller,
wherein the one or more processors are configured to receive an environmental signal from the detector circuit of the environmental sensor system indicative of the at least one analyte gas.

18. The unmanned vehicle system of claim 17, wherein the environmental sensor system has a weight in a range between 0.005 grams and 1 gram.

19. The unmanned vehicle system of claim 17, further comprises a vehicle battery electrically coupled to the at least one motor.

20. The unmanned vehicle system of claim 19, wherein the environmental sensor system includes a detector battery electrically coupled to the detector circuit separate from the vehicle battery.

21. The unmanned vehicle system of claim 17, further comprising a global positioning system electrically coupled to the vehicle controller, and an electronic speed controller electrically coupled to the at least one motor.

22. A method of collecting environmental conditions comprising:
positioning an unmanned vehicle system including an environmental sensor system to detect an environmental condition;
applying electrical stimuli at multiple frequency ranges to the environmental sensor system, the environmental sensor system comprising a non-resonant sensor that includes a sensing element and a detector circuit, wherein the sensing element includes a sensing material and electrodes;
measuring, via the detector circuit of the non-resonant sensor, one or more impedance responses of the sensing element at one or more frequencies of the multiple frequency ranges during exposure of the sensing material to at least one analyte gas, wherein the detector circuit is configured to detect and quantify the at least one analyte gas, and wherein the detector circuit comprises one or more passive electrical components configured to be electrically coupled to the sensing element; and
electrically coupling, via the detector circuit of the non-resonant sensor, the one or more passive electrical components to the sensing element, electrically decoupling, via the detector circuit of the non-resonant sensor, the one or more passive electrical components from the sensing element, or both, to control the one or more frequencies of the one or more impedance responses of the sensing element corresponding to one or more of a low detection range of the sensing material to the at least one analyte gas, a high detection range of the sensing material to the at least one analyte gas, an impedance response linearity of the sensing material to the at least one analyte gas, a dynamic range of measurements of the at least one analyte gas by the sensing material, or a rejection of one or more interfering gases by the sensing material with the detector circuit.

23. The method of claim 22, wherein positioning the unmanned vehicle system includes flying the unmanned vehicle system to a predetermined position.

24. The method of claim 22, wherein positioning the unmanned vehicle system includes pivoting a propeller of an aquatic vehicle.

25. The method of claim 22, wherein positioning the unmanned vehicle system includes steering the unmanned vehicle system based on an operation signal received by a control unit coupled to the unmanned vehicle system.

26. The method of claim 22, wherein positioning the unmanned vehicle system includes steering the unmanned vehicle system based on a detector signal received from the detector circuit.

27. An unmanned vehicle system comprising:
an environmental sensor system configured to detect one or more environmental conditions of an environment in operational contact with the unmanned vehicle system, the environmental sensor system comprising a non-resonant sensor that includes:
a sensing element that includes a sensing material and electrodes configured to apply electrical stimuli to the sensing material at multiple frequency ranges; and
a detector circuit configured to detect and quantify at least one analyte gas by measuring one or more impedance responses of the sensing element at one or more frequencies of the multiple frequency ranges during exposure of the sensing material to the at least one analyte gas, wherein the detector circuit comprises one or more passive electrical components configured to be electrically coupled to the sensing element,
wherein the detector circuit is configured to electrically couple the one or more passive electrical components to the sensing element, electrically decouple the one or more passive electrical components from the sensing element, or both, to control the one or more frequencies of the one or more impedance responses of the sensing element corresponding to one or more of a low detection range of the sensing material to the at least one analyte gas, a high detection range of the sensing material to the at least one analyte gas, an impedance response linearity of the sensing material to the at least one analyte gas, a dynamic range of measurements of the at least one analyte gas by the sensing material, or a rejection of one or more interfering gases by the sensing material; and one or more processors are configured to:
receive a detector signal from the detector circuit of the environmental sensor system indicative of the one or more environmental conditions and
position the unmanned vehicle system during a predetermined period of data acquisition.

28. The unmanned vehicle system of claim 27, wherein to position the unmanned vehicle system during the predetermined period of data acquisition the one or more processors are configured to dynamically control movement based on the detector signal from the detector circuit.

29. The unmanned vehicle system of claim 27, wherein to position the unmanned vehicle system during the predetermined period of data acquisition the one or more processors are configured to dynamically control movement based on detected route condition signals.

30. The unmanned vehicle system of claim 27, wherein to position the unmanned vehicle system during the predetermined period of data acquisition the one or more processors are configured to dynamically control movement based on instructions received in a vehicle controller including a predetermined flight path.

31. The unmanned vehicle system of claim 27, wherein to position the unmanned vehicle system during the predetermined period of data acquisition the one or more processors are configured to dynamically control movement based on detected route condition signals and the detector signal from the detector circuit.

32. The unmanned vehicle system of claim 27, wherein to position the unmanned vehicle system during the predetermined period of data acquisition the one or more processors are configured to prevent movement during the predetermined period.

33. The unmanned vehicle system of claim 27, wherein to position the unmanned vehicle system during the predetermined period of data acquisition the one or more processors are configured to control movement based on operation signals of a remote device.

34. The unmanned vehicle system of claim 27, wherein to position the unmanned vehicle system during the predetermined period of data acquisition the one or more processors are configured to dynamically control movement based on historical data stored in a memory.

35. The unmanned vehicle system of claim 34, wherein the one or more processors are configured to:
store environmental data of the detector signal in the historical data of the memory during the predetermined period of data acquisition.

36. The unmanned vehicle system of claim 35, wherein the one or more processors are configured to:
transmit the environmental data of the detector signal in the historical data to a remote device.

37. The unmanned vehicle system of claim 35, wherein the one or more processors are configured to:
display the environmental data of the detector signal in the historical data.

* * * * *